US00RE50715E

(19) United States
(12) Reissued Patent
Bowie et al.

(10) Patent Number: US RE50,715 E
(45) Date of Reissued Patent: Dec. 30, 2025

(54) SYNTHETIC BIOCHEMISTRY MOLECULAR PURGE VALVE MODULE THAT MAINTAIN CO-FACTOR BALANCE

(71) Applicant: The Regents of the University of California, Oakland, CA (US)

(72) Inventors: James U. Bowie, Culver City, CA (US); Paul H. Opgenorth, Los Angeles, CA (US); Tyler P. Korman, Sierra Madre, CA (US)

(73) Assignee: The Regents of the Univesity of California, Oakland, CA (US)

(21) Appl. No.: 18/052,136

(22) Filed: Nov. 2, 2022

Related U.S. Patent Documents

Reissue of:
(64) Patent No.: 10,822,623
Issued: Nov. 3, 2020
Appl. No.: 16/243,332
Filed: Jan. 9, 2019

U.S. Applications:
(63) Continuation of application No. 15/127,351, filed as application No. PCT/US2015/024181 on Apr. 2, 2015, now Pat. No. 10,196,653.

(60) Provisional application No. 61/974,311, filed on Apr. 2, 2014.

(51) Int. Cl.

| | |
|---|---|
| ***C12P 5/00*** | (2006.01) |
| ***C12N 9/02*** | (2006.01) |
| ***C12N 9/10*** | (2006.01) |
| ***C12P 7/625*** | (2022.01) |

(52) U.S. Cl.
CPC ..... *C12P 5/007* (2013.01); *C12N 9/0008* (2013.01); *C12N 9/1029* (2013.01); *C12P 7/625* (2013.01); *C12Y 102/01051* (2013.01); *C12Y 106/99001* (2013.01); *C12Y 108/01004* (2013.01); *C12Y 203/01012* (2013.01)

(58) Field of Classification Search
None
See application file for complete search history.

(56) References Cited

U.S. PATENT DOCUMENTS

| | | | | |
|---|---|---|---|---|
| 10,196,653 | B2 * | 2/2019 | Bowie | C12P 102/01051 |
| 2005/0048596 | A1 * | 3/2005 | Kristian | G01N 33/5079 435/25 |
| 2013/0030164 | A1 * | 1/2013 | Yoshida | C12Y 106/03001 435/254.2 |
| 2014/0058056 | A1 | 2/2014 | Burgard et al. | |
| 2014/0342419 | A1 * | 11/2014 | Dischert | C12N 15/52 435/158 |
| 2014/0377798 | A1 * | 12/2014 | Ertl | C12P 19/36 435/52 |

FOREIGN PATENT DOCUMENTS

WO 2010/051527 A2 5/2010

OTHER PUBLICATIONS

Lopez de Felipe, F., et al. J. Bacteriol. (1998), 180(15); 3804-3808.*
Hawkins, C. F., et al. Eur. J. Biochem (1990), 191; 337-346.*
Merriam-Webster's Cllegiate Dictionary (2002), Tenth Edition; "unbalanced" definition.*
Berrios-Rivera et al., "Metabolic engineering of *Escherichia coli*: increase of NADH availability by overexpressing an NAD+-dependent formate dehydrogenase", Metabolic Engineering, Jul. 2002, vol. 4(3), pp. 217-229.
Bologna et al., "*Escherichia coli* Malic Enzymes: Two Isoforms with Substantial Differences in Kinetic Properties, Metabolic Regulation, and Structure", Journal of Bacteriology, Aug. 2007, pp. 5937-5946.
Heux et al., "Cofactor engineering in *Saccharomyces cerevisiae*: Expression of H2O-forming NADH oxidase and impact on redox metabolism", Metabolic Engineering, 8:4, Jul. 1, 2006 (published online Feb. 10, 2006), pp. 303-314.
Nickitas-Etienne, International Preliminary Report on Patentability and Written Opinion, PCT/US2015/024181, The International Bureau of WIPO, Oct. 13, 2016.
Niebuhr-Ebel, K., Extended European Search Report, Application No. 15774454.1, European Patent Office, Jul. 17, 2017.
Niebuhr-Ebel, K., Extended European Search Report, European Patent Office, Application No. 19212269.5, Jan. 30, 2020.
Nikel et al., "Redox driven metabolic tuning", Bioengineered Bugs, Jul. 1, 2010, 1(4), pp. 291-295.
Opgenorth et al., "A synthetic biochemistry molecular purge valve module that maintains redox balance," Nat. Commun., Jun. 17, 2014, vol. 5, Article No. 4113, 8 pages.
Thomas, Shane, International Search Report and Written Opinion, PCT/US2015/024181, United States Patent and Trademark Office, Sep. 18, 2015.
Korman et al., "A synthetic biochemistry system for the in vitro production of isoprene from glycolysis intermediates", Protein Science, 23:5, Mar. 12, 2014 (published online Feb. 6, 2014), pp. 576-585.
Satoh et al., "Enzyme-catalyzed poly(3-hydroxybutyrate) synthesis from acetate with CoA recycling and NADPH regeneration in vitro", Journal of Bioscience of Bioengineering, 95:4, Jan. 1, 2003, pp. 335-341.
Korman Tyler P. et al., "A synthetic biochemistry platform for cell free production of monoterpenes from glucose", Nature Communications, vol. 8, No. 1, Aug. 1, 2017, pp. 1-8.
Niebuhr-Ebel, K., Extended European Search Report, European Patent Office, Application No. 19212269.5, dated Jan. 30, 2020.
Opgenorth et al., "A synthetic biochemistry module for production of bio-based chemicals from glucose", Nature Chemical Biology, vol. 12, No. 6, Jun. 1, 2016, pp. 393-395.
Opgenorth et al., "A molecular rheostate maintains ATP levels to drive a synthetic biochemistry system", Nature Chemical Biology, vol. 13, No. 9, Sep. 1, 2017, pp. 938-942.

* cited by examiner

*Primary Examiner* — Kevin S Orwig
(74) *Attorney, Agent, or Firm* — Gavrilovich, Dodd & Lindsey LLP

(57) ABSTRACT

The disclosure provides a metabolic pathway for producing a metabolite, the metabolic pathway having a co-factor purge valve system for recycling a cofactor used in the metabolic pathway.

20 Claims, 7 Drawing Sheets

Specification includes a Sequence Listing.

| | | NAD+ | | NADH | |
|---|---|---|---|---|---|
| | | 0.1 mM | 1 mM | 0.1 mM | 1 mM |
| | | Relative Yield | Relative Yield | Relative Yield | Relative Yield |
| NADP+ | 0.1 mM | 93.01 ± 0.77 | 91.87 ± 2.13 | 91.87 ± 1.71 | 93.79 ± 2.97 |
| | 1 mM | 106.53 ± 6.21 | 115.12 ± 5.27 | 114.50 ± 5.42 | 109.48 ± 1.70 |
| NADPH | 0.1 mM | 108.29 ± 2.45 | 89.69 ± 0.53 | 86.38 ± 1.56 | 90.37 ± 4.91 |
| | 1 mM | 93.99 ± 4.33 | 108.13 ± 2.00 | 106.16 ± 4.52 | 100.62 ± 1.64 |

SYNTHETIC BIOCHEMISTRY MOLECULAR PURGE VALVE MODULE THAT MAINTAIN CO-FACTOR BALANCE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application *is a reissue application of U.S. Pat. No. 10,822,623, which issued on Nov. 3, 2020, from U.S. patent application Ser. No. 16/243,332, filed Jan. 9, 2019, which* is a continuation of U.S. patent application Ser. No. 15/127,351, filed Sep. 19, 2016, which claims priority to International Application No. PCT/US2015/024181, filed Apr. 2, 2015, which application claims priority to U.S. Provisional Application Ser. No. 61/974,311, filed Apr. 2, 2014, the disclosures of which are incorporated herein by reference.

STATEMENT REGARDING FEDERALLY SPONSORED RESEARCH

This invention was made with government support under Grant Number DE-FC02-02ER63421, awarded by the U.S. Department of Energy. The government has certain rights in the invention.

*INCORPORATION BY REFERENCE OF SEQUENCE LISTING*

*Accompanying this filing is a Sequence Listing entitled "00011-077USRE.xml", created on Nov. 2, 2022 and having 32,136 bytes of data, machine formatted on IBM-PC, MS-Windows operating system. The sequence listing is hereby incorporated by reference in its entirety for all purposes.*

TECHNICAL FIELD

The disclosure provides engineered pathways for chemical production using a cofactor balancing molecular purge system.

BACKGROUND

The greatest potential environmental benefit of metabolic engineering would be the production of low value/high volume commodity chemicals, such as biofuels. Yet the high yields required for the economic viability of low-value chemicals is particularly hard to achieve in microbes due to the myriad competing biochemical pathways needed for cell viability.

SUMMARY

The disclosure provides a recombinant, artificial or engineered metabolic pathway comprising a plurality of enzymatic steps that converts a substrate to a product, wherein the pathway includes an unbalanced production and utilization of a co-factor the pathway comprising a non-naturally occurring purge valve pathway that recycles the co-factor, wherein the purge valve pathway comprises an enzyme that uses the co-factor to convert a metabolite in one or more of the plurality of enzymatic steps. In one embodiment, the recombinant, artificial or engineered metabolic pathway comprises (a) a first enzymatic step that converts a first metabolite to a second metabolite using a first co-factor; (b) a second enzymatic step that converts the first metabolite to the second metabolite using a second co-factor; and (c) a third enzymatic step that converts the second or a third metabolite to an intermediate or the product using the second cofactor; wherein when the co-factor utilization become unbalanced between the first and second cofactor, the purge valve pathway purges the excess co-factor. In a further embodiment of either of the foregoing the co-factors are oxidizing/reducing co-factors. In a further embodiment, the oxidizing/reducing co-factors are $NAD^+$/NADH, $NADP^+$/NADPH or $FAD^+$/FADH. In another embodiment of any of the foregoing the first cofactor comprises $NAD^+$/NADH and the second cofactor comprises $NADP^+$/NADPH. In another embodiment of any of the foregoing the purge valve pathway comprises a NADH dehydrogenase, and NADPH dehydrogenase and an NADH oxidase. In a further embodiment, the NADH dehydrogenase is a NADH pyruvate dehydrogenase complex. In still a further embodiment, the NADH pyruvate dehydrogenase complex comprises a pyruvate dehydrogenase subunit a, a pyruvate dehydrogenase subunit b, a dihydrolipoamide acetyltransferase, and a dihydrolipoamide dehydrogenase. In yet a further embodiment, the pyruvate dehydrogenase subunit a comprises a sequence that is at least 90%, 91%, 92%, 93%, 94%, 95%, 96%, 97%, 98%, 99% or 100% identical to SEQ ID NO:1, wherein the pyruvate dehydrogenase subunit b comprises a sequence that is at least 90%, 91%, 92%, 93%, 94%, 95%, 96%, 97%, 98%, 99% or 100% identical to SEQ ID NO:2, wherein the dihydrolipoamide acetyltransferase is at least 90%, 91%, 92%, 93%, 94%, 95%, 96%, 97%, 98%, 99% or 100% identical so SEQ ID NO:3, and wherein the dihydrolipoamide dehydrogenase is at least 90%, 91%, 92%, 93%, 94%, 95%, 96%, 97%, 98%, 99% or 100% identical to SEQ ID NO:5, wherein the complex converts pyruvate to acetyl-CoA. In yet a further embodiment, the NADPH dehydrogenase is a NADPH pyruvate dehydrogenase complex. In a further embodiment, the NADPH pyruvate dehydrogenase complex comprises a pyruvate dehydrogenase subunit a, a pyruvate dehydrogenase subunit b, a dihydrolipoamide acetyltransferase, and a mutant dihydrolipoamide dehydrogenase the preferentially uses $NADP^+$. In another embodiment, the pyruvate dehydrogenase subunit a comprises a sequence that is at least 90%, 91%, 92%, 93%, 94%, 95%, 96%, 97%, 98%, 99% or 100% identical to SEQ ID NO:1, wherein the pyruvate dehydrogenase subunit b comprises a sequence that is at least 90%, 910, 92%, 93%, 94%, 95%, 96%, 97%, 98%, 99% or 100% identical to SEQ ID NO:2, wherein the dihydrolipoamide acetyltransferase is at least 900, 910, 920, 930, 940, 950, 960, 970, 980, 990 or 100% identical so SEQ ID NO:3, and wherein the dihydrolipoamide dehydrogenase is at least 900, 910, 920, 930, 940, 950, 960, 970, 980, 990 or 100% identical to SEQ ID NO:7 and preferentially uses $NADP^+$, wherein the complex converts pyruvate to acetyl-CoA. In yet further embodiments, the NADH oxidase is a NoxE or homolog thereof. In a further embodiment, the NADH oxidase comprises a sequence that is at least 900, 910, 920, 930, 940, 950, 960, 970, 980, 990 or 100% identical to SEQ ID NO:10. In another embodiment of any of the foregoing the pathway is a cell-free system. In still another embodiment, the recombinant, artificial or engineered pathway produces PHB. In yet another embodiment, the recombinant, artificial or engineered pathway produces isoprene.

The disclosure also provides an enzymatic system comprising a metabolic pathway including a plurality of enzymes for converting a substrate to a product, the metabolic pathway having an unbalanced utilization of reducing/oxidizing cofactors, wherein the enzymatic system comprises a metabolic purge valve comprising an NADH pyruvate dehydrogenase, and NADPH pyruvate dehydrogenase and a NADH/NADPH oxidase.

The disclosure also provides a recombinant microorganism comprising a heterologous NADH pyruvate dehydrogenase, a NADPH pyruvate dehydrogenase and a NADH and/or NADPH oxidase.

The disclosure also provides a recombinant polypeptide comprising a sequence that is at least 900, 910, 920, 930, 940, 950, 960, 970, 980, 990 or 100% identical to SEQ ID NO:5 and comprising the mutations E206V, G207R, A208K, and S213R. In one embodiment, the polypeptide comprises the sequence of SEQ ID NO:7.

The disclosure also provides a polynucleotide encoding a polypeptide comprising a sequence that is at least 900, 910, 920, 930, 940, 950, 960, 970, 980, 990 or 100% identical to SEQ ID NO:5 and comprising the mutations E206V, G207R, A208K, and S213R. In a further embodiment, the polynucleotide encodes a polypeptide of SEQ ID NO:7. In a further embodiment, the polynucleotide comprises a sequence that is 70-90%, 91%, 92%, 93%, 94%, 95%, 96%, 97%, 98%, 990 or 100% identical to SEQ ID NO:6 and encodes a polypeptide of SEQ ID NO:7.

The disclosure provides a recombinant, artificial or engineered pathway that converts a substrate to a desired product, wherein the pathway includes an unbalanced production and utilization of a cofactor the pathway comprising a first metabolic step that produces a first reduced cofactor and a second metabolic step that oxidizes the first reduced cofactor, wherein the pathway comprises a purge valve pathway that recycles a second reduced cofactor. In one embodiment, the first reduced cofactor comprises NADPH and the second reduced cofactor comprises NADH. In a further embodiment, the purge valve pathway comprises a NADH dehydrogenase and an NADH oxidase. In still a further embodiment, the NADH dehydrogenase is a NADH pyruvate dehydrogenase. In another embodiment, the first reduced cofactor comprises NADH and the second reduced cofactor comprises NADPH. In yet another embodiment, the purge valve pathway comprises a NADPH dehydrogenase and an NADPH oxidase. In a further embodiment, the NADPH dehydrogenase is a NADPH pyruvate dehydrogenase. In another embodiment of any of the foregoing claims the pathway produces isoprene from pyruvate. In yet another embodiment of any of the foregoing claims the pathway produces PHB.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

No purge valve was used in the first reaction ($PDH^{NADH}$, NADPH, NoxE). NADPH was simply added and NADH recycled using NoxE. The final experiment ($PDH^{NADH}$, $PDH^{NADPH}$, NoxE) shows results employing the full purge valve system. Leaving out any component of the purge valve system resulted in dramatic decreases in isoprene production. Each reaction was performed in duplicate.

Figure 7:
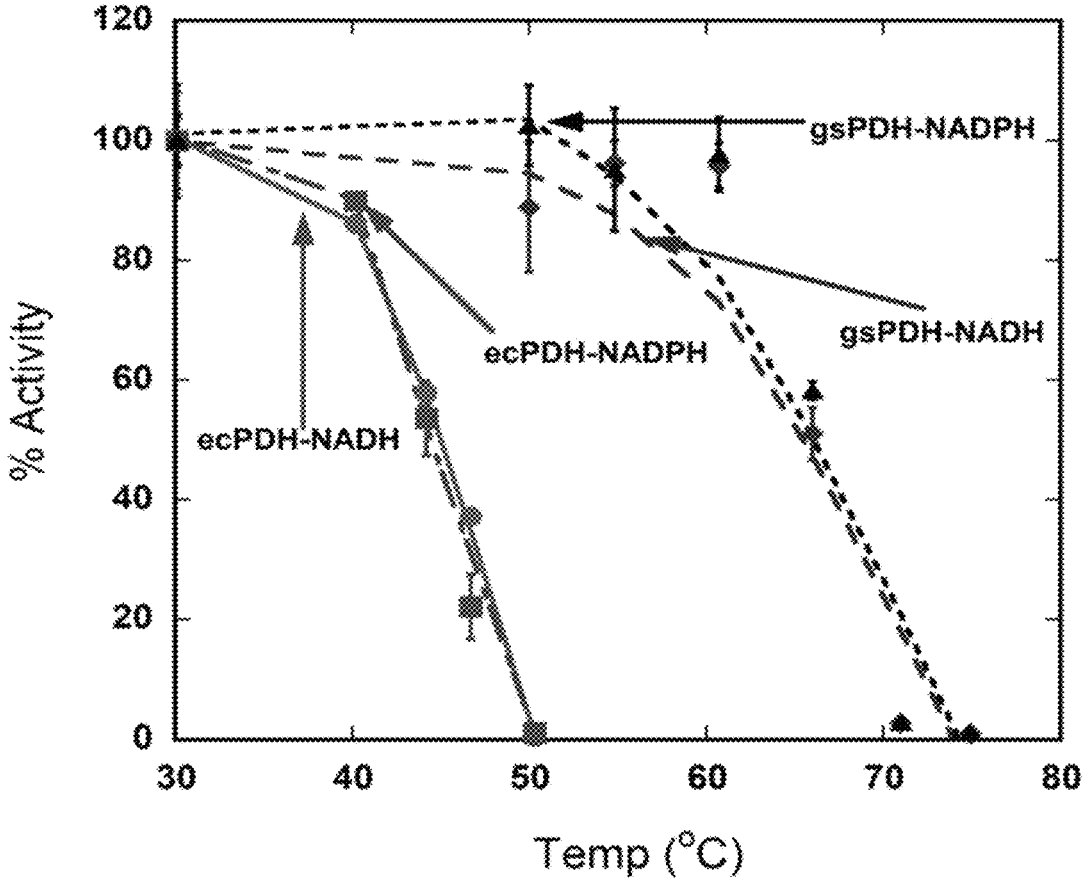

FIG. 7 shows the stability of the GsPDH enzymes. Enzymes were incubated at a given temperature for 1 hour and then immediately assayed for activity.

Figure 8:
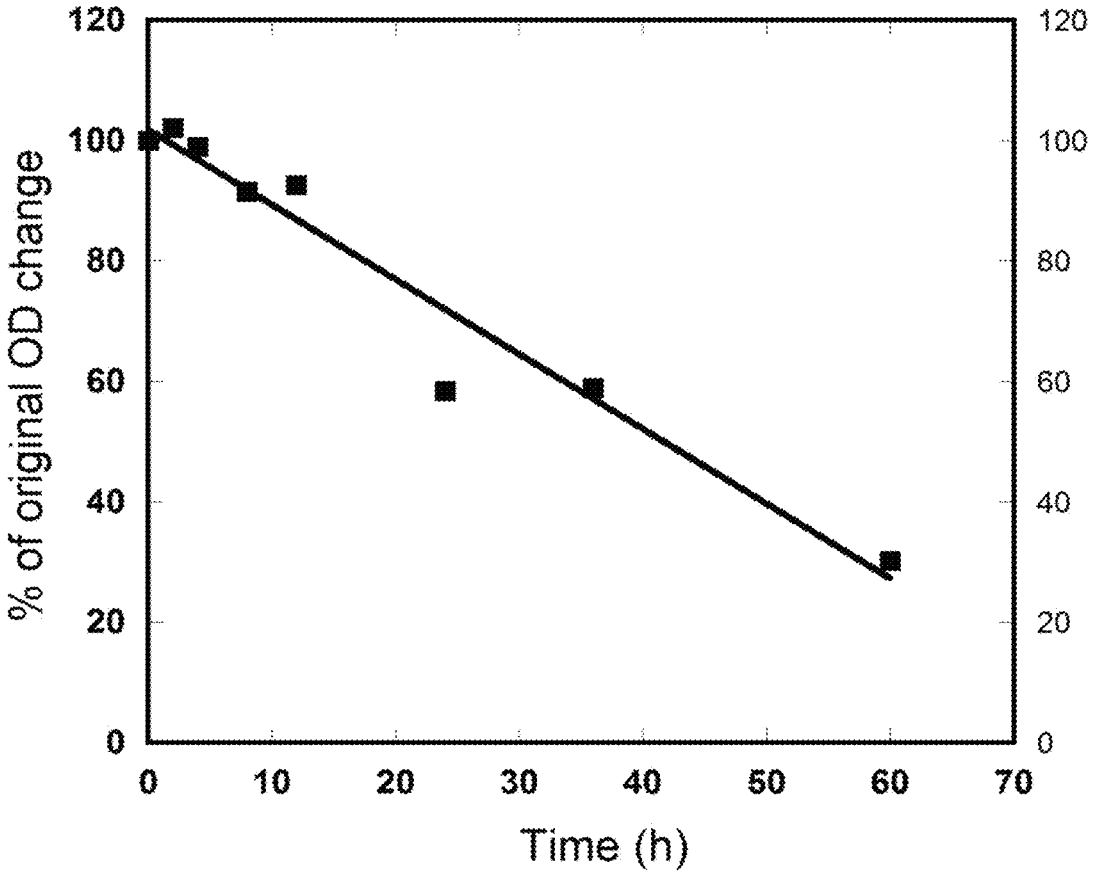

FIG. 8 shows the stability of the PHB system at room temperature. All the components of the optimized PHB system were mixed, leaving out pyruvate and then the system was incubated at room temperature. At various times the reaction was initiated by the addition of pyruvate and the extent of the reaction monitored by the final $OD_{600}$. The plot shows the percent extent of reaction achieved for each pre-incubation time.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the enzyme" includes reference to one or more enzymes, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product. The disclosure provides in vitro biosynthetic pathways comprising a metabolic purge vale as well as providing recombinant microorganism having a metabolically engineered pathway comprising a metabolic purge valve for the production of a desired product or intermediate.

As used herein a "cofactor" generally refers to a chemical compound or metabolite that is required for a protein's biological activity. These proteins are commonly enzymes, and cofactors assist in biochemical transformations. Cofactors include, but are not limited to, one or more inorganic ions, or a complex organic or metalloorganic molecule sometimes referred to as a coenzyme; most of which are derived from vitamins and from required organic nutrients in small amounts. Some enzymes or enzyme complexes require several cofactors. For example, the multienzyme complex pyruvate dehydrogenase at the junction of glycolysis and the citric acid cycle requires five organic cofactors and one metal ion: loosely bound thiamine pyrophosphate (TPP), covalently bound lipoamide and flavin adenine dinucleotide (FAD), and the cosubstrates nicotinamide adenine dinucleotide ($NAD^+$) and coenzyme A (CoA), and a metal ion ($Mg^{2+}$). Organic cofactors are often vitamins or are made from vitamins. Many contain the nucleotide adenosine monophosphate (AMP) as part of their structures, such as ATP, coenzyme A, FAD, and $NAD^+$.

An "enzyme" means any substance, typically composed wholly or largely of amino acids making up a protein or polypeptide that catalyzes or promotes, more or less specifically, one or more chemical or biochemical reactions.

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., a carbohydrate, a sugar phosphate, pyruvate etc.), an intermediate in (e.g., acetyl-coA), or an end product (e.g., isoprene or PHB) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

As used herein, the term "metabolically engineered" or "metabolic engineering" involves rational pathway design and assembly of biosynthetic genes, genes associated with operons, and control elements of such polynucleotides, for the production of a desired metabolite, such as acetyl-CoA, higher alcohols or other chemical, in a microorganism or in vitro. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolic purge valve" refers to an engineered metabolic pathway that 'purges' excess metabolites and/or co-factors resulting in a recycling of the metabolite or co-factor for use in a primary metabolic pathway.

The term "polynucleotide," "nucleic acid" or "recombinant nucleic acid" refers to polynucleotides such as deoxyribonucleic acid (DNA), and, where appropriate, ribonucleic acid (RNA).

A "protein" or "polypeptide", which terms are used interchangeably herein, comprises one or more chains of chemical building blocks called amino acids that are linked together by chemical bonds called peptide bonds. A protein or polypeptide can function as an enzyme.

The term "recombinant microorganism" and "recombinant host cell" are used interchangeably herein and refer to microorganisms that have been genetically modified to express or over-express endogenous polynucleotides, or to express non-endogenous sequences, such as those included in a vector. The polynucleotide generally encodes a target enzyme involved in a metabolic pathway for producing a desired metabolite as described herein, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway as described herein. In addition, a substrate can be an oxidized or reduced co-factor or a factor that is phosphorylated or de-phosphorylated.

Metabolic engineering and synthetic biology have been employed for the production of high value chemicals but have not been as successful as hoped in meeting the stringent economics of large scale commodity chemical manufacturing. Microbial systems are often hampered by a variety of technical challenges that make it hard to achieve cost competitiveness, including poor yields due to competing pathways; low productivity caused by slow growth rates or difficulties in pathway optimization; contaminating microbial growth; product toxicity; and expensive product isolation.

One approach that is beginning to receive attention is to perform complex biochemical transformations using mixtures of enzymes in a reaction vessel or flow system rather than within a cell. Building single, dedicated pathways in vitro can eliminate side reactions that occur in the cell, so that nearly 100% yields and fast reaction times are possible. In vitro biochemical systems also allow for more precise control over optimization and product toxicity problems can be more easily diagnosed and mitigated. Moreover, product extraction can be more facile.

Traditionally, in vitro pathway construction has been relegated to use as a research tool or in applications that require only 1-3 enzymes for the production of chiral compounds and other high value chemicals. Improvements in protein expression and access to stable enzymes have made more complex systems possible. In vitro biotransformation systems have been reported in recent years involving systems of over thirty enzymes. One of the first modern studies in this area was an artificial pathway that produced hydrogen from starch. The concept was recently advanced with a creative system that generated hydrogen from cellobiose at nearly 100% yields. In another effort, hyper-thermophilic glycolysis enzymes were heterologously expressed, heat purified, and assembled to convert glucose to n-butanol in 82% yield. In another study, an elegantly simplified non-phosphorylative Entner-Doudoroff pathway from hyper-thermophilic archaea was constructed to produce ethanol and isobutanol in 55% yields. These pioneering studies illustrate the flexibility of synthetic biochemistry and the potential for high yields.

Maintaining proper cofactor balance is an essential part of generating flux and providing a driving force through an enzymatic pathway. In vivo, the enzymatic specificity for the cofactors NADH and NADPH are typically used to control the carbon flux through catabolic and anabolic pathways respectively. Organisms typically sense the reduction state of these cofactors and use this information to up-regulate or down-regulate catabolic and anabolic pathways to cope with environmental changes. In vitro systems, however, do not have the myriad of peripheral pathways that facilitate this control. Moreover, the natural anabolic and catabolic specificities for NADH and NADPH complicate in vitro biotransformations. Synthetic biochemistry systems have often dealt with these problems by careful considerations of cofactor stoichiometry in pathway design, through the use of expensive sacrificial metabolites, reengineering enzymes so that only a single cofactor type is needed, adding excess cofactors, or constantly adding intermediates to the reaction mix to sustain the process.

Although the methods, compositions and systems described herein are described with reference to certain metabolic products, the methods, compositions and systems are applicable to a broad range of recombinant biochemical pathways were co-factor recycling is important. In one exemplary engineered pathway the disclosure describes the production of polyhydroxybutyrates (PHBs) and polyhydroxyalkanoates (PHAs). In another exemplary embodiment, the disclosure describes the production of isoprene. Both embodiments utilize a molecular purge valve system of the disclosure to maintain appropriate co-factor balance.

PHBs and other PHAs are biodegradable thermoplastics. PHAs can have characteristics similar to many popular petrochemical derived polymers, but are nontoxic and biodegradable, thus these compositions are attracting increased attention as a possible green alternative to petroleum based polymers in a wide range of applications. The best characterized and most abundant PHA polymer is polyhydroxybutyrate (PHB) that is naturally produced from Acetyl-CoA as a carbon and energy storage mechanism in many organisms. Currently, industrial production of PHB is done by in vivo batch culture processes under nutrient starvation. This process is typically very time consuming, requires large fermentation volumes, and requires expensive methods for the extraction of PHB. Prior attempts to produce bioplastic in vitro have required the addition of sacrificial substrates and a molar excess of cofactors to convert acetate to PHB.

Isoprene is a platform chemical for a variety of products, but it is mostly employed in the production of synthetic rubber. The isoprenoid pathway also provides precursors for over 25,000 known biomolecules including drugs such as taxol and potential biofuels. There have been a number of efforts to produce isoprene in microorganisms and the best reported yield is 28% from glucose. Korman et al. (Protein Sci., 23(5):576-85, May 2014), showed that a synthetic biochemistry system could produce isoprene in >95% yield from pyruvate as long as high energy cofactors were added. Examples of isoprenoids that can be produced by the methods, compositions and systems of the disclosure are selected from the group consisting of a hemiterpene, monoterpene, diterpene, triterpene, tetraterpene, sesquiterpene, and polyterpene. For example, the isoprenoid can be selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

The disclosure describes a purge valve system for cofactor balance in in vitro pathways for chemical production and in vivo systems. For example, the disclosure describes a pathway to convert pyruvate into PHB that maintains sustainable reducing cofactor balance, without the requirement for perfect stoichiometric matching of cofactor generation and usage to carbon usage. Further, the disclosure described the use of the molecular purge valve system in other pathways. For example, the disclosure demonstrates the purge valve system can be used as the basis for the production of other Acetyl-CoA derived products by applying it to the production of isoprene from pyruvate via the mevalonate pathway. Thus, the regulatory modules described herein can free us from having to perfectly balance cofactor utilization when designing synthetic biochemistry systems.

The disclosure provides a robust node of control to balance the production and consumption of cofactors such as NADPH and NADH in a self-regulating and self-balancing manner. This in vitro pathway maintains cofactor balance without requiring adherence to stoichiometry in the generation and utilization of cofactors to ensure carbon flux. In part because the system can sustain high levels of NADPH, driving the transformation to near completion, converting for example, pyruvate to either PHB or isoprene at nearly 100% of the theoretical yield. Moreover, the high yields in the system are robust to 10-fold variations in cofactor levels.

Ultimately the methods and compositions of the disclosure can be expanded to incorporate the conversion of low cost substrates such as glucose or other sugars into pyruvate, which would involve the glycolysis pathway or parts of the glycolysis pathway. Indeed a synthetic biochemistry system employing glycolysis has been demonstrated previously. Building more complex compounds from Acetyl-CoA such as fatty acids, polyketides, and other isoprenoids incorporate the use and recycling of ATP. In such instances developing a regulatory systems like the purge valve employed here, will free synthetic biochemistry system design from having to consume the high energy cofactors during the anabolic phase in perfect stoichiometric balance. Thus, the approach can help diversify the chemical targets of synthetic biochemistry.

The biotransformation of pyruvate into PHB, illustrates a basic co-factor imbalance problem that is encountered in biochemical systems. In particular, conversion of pyruvate to Acetyl-CoA by pyruvate dehydrogenase (PDH) yields one molecule of NADH. However, the three enzyme pathway (phaA, B, and C) to PHB from Acetyl-CoA utilizes only one half a molecule of NADPH per Acetyl-CoA. Thus, the canonical pathway produces an excess of reducing equivalents. Moreover, the reducing equivalents are of the wrong type (NADH rather than NADPH). The disclosure exemplifies the purge valve system in a pathway for the regulation of NAD and NADP and their reduced equivalents, shown in FIG. 1A, that can generate the correct cofactor and regulate its production.

Figure 1:
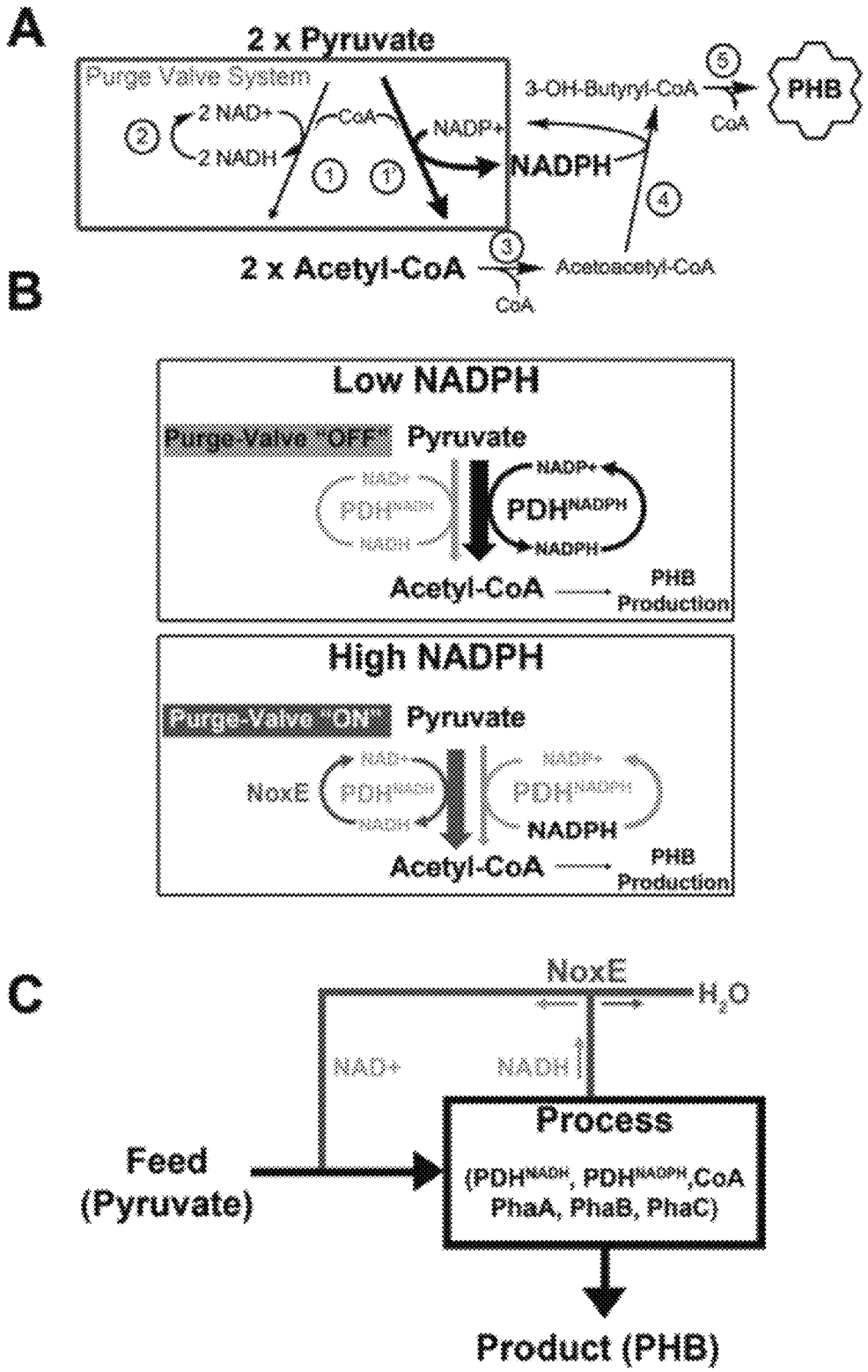
FIG. 1A-C shows a synthetic biochemistry purge valve system for the production of PHB. (A) The in vitro metabolic pathway for the conversion of pyruvate to PHB. The pathway comprises 6 separate reactions: reaction 1 ($PDH^{NADH}$), reaction 2 ($PDH^{NADPH}$), reaction 3 (NoxE), reaction 4 (PhaA), reaction 5 (PhaB), reaction 6 (PhaC). The purge valve is highlighted in the boxed pathway. (B) How the purge valve is designed to function. At low NADPH (high NADP+), $PDH^{NADPH}$ reaction dominates, generating Acetyl-CoA and NADPH from pyruvate and $NADP^+$. The purge valve is effectively "off". In high NADPH (low $NADP^+$) conditions, the $PHD^{NADPH}$ enzyme is starved for oxidized cofactor, shutting down the pathway to Acetyl-CoA. In this situation, the $PDH^{NADH}$/NoxE system takes over, producing Acetyl-CoA; the purge valve is "on". (C) An exemplary chemical engineering schematic of the purge valve system used in the production of PHB from pyruvate, involving a cofactor recycle loop.

In the design, a synthetic biochemistry "purge valve" was developed that effectively decouples the stoichiometric production of NAD(P)H from Acetyl-CoA (FIG. 1). To this end a mixture of both an $NAD^+$-utilizing wild-type PDH ($PDH^{NADH}$), a mutant PDH that utilizes $NADP^+$ ($PDH^{NADPH}$), and a water generating NADH oxidase (NoxE) that specifically oxidizes NADH, but not NADPH was utilized. By employing this metabolic node, NADPH was generated for PHB production from pyruvate, but also dissipate excess reducing equivalents in an auto-regulatory manner. As illustrated in FIG. 1B, under low NADPH, high $NADP^+$ conditions, the mutant $PDH^{NADPH}$ can operate to generate Acetyl-CoA and restore NADPH levels. Under high NADPH, low $NADP^+$ conditions, the $PDH^{NADPH}$ activity will automatically be choked off, and the wild-type $PDH^{NADH}$ will be used preferentially to produce Acetyl-CoA and NADH. In this high NADPH condition, the reducing equivalents are not needed. Because the reducing equivalents are produced in the form of NADH and not NADPH, they are eliminated by an oxidase, NoxE. The presence of NoxE ensures that NADH never builds up and the $PDH^{NADH}$ can always operate to generate carbon for the PHB pathway in the form of Acetyl-CoA. The $PDH^{NADH}$/$PDH^{NADPH}$/NoxE system acts like a purge valve that opens under conditions of high NADPH to relieve the excess reducing equivalent "pressure" (i.e. buildup of NADH) and allow carbon flux to be maintained. An engineering schematic of the purge valve system is shown in FIG. 1C.

For example, the disclosure demonstrates that to construct an in vitro system the enzymes were acquired commercially or purified, tested for activity, and mixed together in a properly selected reaction buffer. The system comprises a core set of enzymes for the "purge valve" system and a secondary set of enzyme for the synthesis of a desired chemical or biofuel. The core purge valve system can be utilized in combination with any in vitro system that converts one set of metabolites (e.g., a first carbon source) to a second metabolite (e.g., a desired chemical product), wherein the secondary metabolic pathway (e.g., the product pathway) uses or produces and excess of co-factor metabolites (e.g., produces an excess of reducing equivalents). In such instances a purge valve system can be utilized to balance the cofactors. For example, in the case of PHB and isoprene these reducing equivalents can be utilized and optimized. In one embodiment, the metabolic pathway produces an excess of a reducing equivalent that is needed for production of the desired product. For example, in Scheme 1, below, a first metabolic step produces reducing equivalents and a second metabolic step utilizes the reducing equivalents, however, the second step uses only a fraction of the reducing equivalents produced in the first step. Thus, in a closed system, the limiting factor will be the reducing equivalents.

Scheme 1

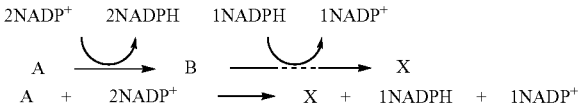

Upon utilization of the available $NADP^+$ in scheme 1, for example, the system would stop and no further metabolites ("B" or "X") would be made. However, in the purge valve system of the disclosure, a secondary pathway that can oxidize the reducing equivalents would become active and allow production of A to B, while still allowing use of the NADPH in steps B to X. Once sufficient enough NADP+ is present then the metabolic pathway from A to B would use the $NADP^+$.

In one embodiment, the purge valve for use in an in vitro system comprises: a combination of both an NADH-dehydrogenase enzyme and an NADPH-dehydrogenase and a NADH or NADPH-oxidase. In one embodiment, the purge valve system comprises an NADH-pyruvate dehydrogenase complex, an NADPH-pyruvate dehydrogenase complex and an NADH-oxidase. It should be noted that other dehydrogenase pairs can be used.

The purge valve system of the foregoing embodiment can be used in combination with any metabolic pathway that produces NADH or NADPH and utilizes a fraction of what was produced in the production of a desired product. For example, the purge system can be used in a pathway that converts pyruvate to acetyl-CoA to produce NADH or NADPH and that utilizes NADH or NADPH to further produce a desired metabolite. Exemplary pathways include the PHB and isoprene pathways described below.

The disclosure provides pathways that can be developed in vitro in a number of ways. For example, the desired enzymes can be cloned/engineered into a microorganism or cell, expressed and then purified from the culture. In another example, the enzymes can be expressed, the cells disrupted and a disrupted preparation used in the pathways of the disclosure. In another embodiment, the enzymes can be purified and tethered to a substrate in a system (e.g., in a microfluidic system) for use in the metabolic pathway. In yet another embodiment, thermophilic enzymes having the desired activity can be cloned, expressed and the cell or preparations therefrom heated to a temperature wherein the desired enzymes remain active while undesired enzymes are denatured. In yet another embodiment, the enzymes can be commercially purchased and mixed as appropriate. In all of the foregoing embodiments, the system would be combined with the necessary substrates and cofactors (e.g., $NAD^-$, $NADP^-$, $FAD^-$, AMP, ADP, ATP and the like).

Accordingly, the disclosure provides "engineered" or "modified" microorganisms that are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. The genetic material introduced into the parental microorganism contains gene(s), or parts of gene(s), coding for one or more of the enzymes involved in a biosynthetic pathway and include gene(s), or parts of gene(s), coding for one or more of the enzymes involved in a metabolic purge valve, the pathway(s) useful for the production of a desired metabolite (e.g., acetyl-phosphate and/or acetyl-CoA), and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products). For example, it may be desirable to engineer an organism to express a desired set for enzymes in a metabolic pathway while eliminating enzymes of competing pathways. This engineering can be applicable for both in vitro (where upon disruption or purification undesirable enzymes are not present) or in vivo.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e. a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a NADH-pyruvate dehydrogenase. This microorganism can act as a parental microorganism in the generation of a microorganism modified to express or over-express a second target enzyme e.g., a NADH-oxidase. As used herein, "express" or "over express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules in to the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells.

The sequence listing appended hereto provide exemplary polynucleotide sequences encoding polypeptides useful in the methods described herein. It is understood that the addition of sequences which do not alter the encoded activity of a nucleic acid molecule, such as the addition of a non-functional or non-coding sequence (e.g., polyHIS tags), is a conservative variation of the basic nucleic acid.

It is understood that a polynucleotide described above include "genes" and that the nucleic acid molecules described above include "vectors" or "plasmids." Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed. The transcribed region of the gene may include untranslated regions, including introns, 5'-untranslated region (UTR), and 3'-UTR, as well as the coding sequence.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for S. cerevisiae and mammals are UAA and UGA, respectively. The typical stop codon for monocotyledonous plants is UGA, whereas insects and E. coli commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

"Transformation" refers to the process by which a vector is introduced into a host cell. Transformation (or transduction, or transfection), can be achieved by any one of a number of means including electroporation, microinjection, biolistics (or particle bombardment-mediated delivery), or agrobacterium mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

The various components of an expression vector can vary widely, depending on the intended use of the vector and the host cell(s) in which the vector is intended to replicate or drive expression. Expression vector components suitable for the expression of genes and maintenance of vectors in E. coli, yeast, Streptomyces, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For E. coli and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For E. coli expression vectors, it is useful to include an E. coli origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997;

Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

In certain embodiments, a metabolic pathway converts a carbon source to a desired intermediate or end product. For example, a carbon source can be converted to pyruvate, which can be metabolized to acetyl-CoA to PHB or isoprene. Suitable carbon sources can be sugars. For example, a carbon source can be a biomass derived sugar. A "biomass derived sugar" includes, but is not limited to, molecules such as glucose, sucrose, mannose, xylose, and arabinose. The term biomass derived sugar encompasses suitable carbon substrates of 1 to 7 carbons ordinarily used by microorganisms, such as 3-7 carbon sugars, including but not limited to glucose, lactose, sorbose, fructose, idose, galactose and mannose all in either D or L form, or a combination of 3-7 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose, and lignin can be generally treated by a variety of chemical, mechanical and enzymatic means to release primarily hexose and pentose sugars. These sugars can then be "fed" into a pathway to produce pyruvate as further described herein.

The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Culture conditions suitable for the growth and maintenance of a recombinant microorganism provided herein are known in the art.

It is understood that a range of microorganisms can be engineered to express one or more enzymes of the disclosure. It is also understood that various microorganisms can act as "sources" for genetic material encoding target enzymes suitable for use in a recombinant microorganism provided herein.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the procaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ([NaCl]); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, Micrococcus, others) (2) low G+C group (Bacillus, Clostridia, Lactobacillus, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; and (11) Thermotoga and Thermosipho thermophiles.

"Gram-negative bacteria" include cocci, nonenteric rods, and enteric rods. The genera of Gram-negative bacteria include, for example, Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, and Fusobacterium.

"Gram positive bacteria" include cocci, nonsporulating rods, and sporulating rods. The genera of gram positive bacteria include, for example, Actinomyces, Bacillus, Clostridium, Corynebacterium, Erysipelothrix, Lactobacillus, Listeria, Mycobacterium, Myxococcus, Nocardia, Staphylococcus, Streptococcus, and Streptomyces.

Accordingly, the disclosure provides an in vitro or in vivo engineered pathway that comprises an NADPH-dehydrogenase (e.g., an NADPH-PDH or homolog thereof), an NADH-dehydrogenase (e.g., an NADPH-PDH or homolog thereof), and an NADH-oxidase (e.g., an NOX or homolog thereof).

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Materials.

Miller LB media or Miller LB-agar (BD Difco) was used for growth of bacterial strains in liquid or solid media. E. coli BL21Gold(DE3) [B, F-, ompT, hsdS$_B$, ($r_B$-,$m_B$-), dcm+, Tetr, galλ, (DE3) endA Hte] (Agilent) was used as host for both cloning and expression of recombinant proteins using pET vectors. E. coli TOP10(DE3) [F-mcrA Δ(mrr-hsdRMS-mcrBC) φ80lacZΔM15 ΔlacX74 nupG recA1 araD139 Δ(ara-leu)7697 galE15 galK16 rpsL(Str$^R$) endA1 λ$^-$] was used for expression of recombinant proteins from the pBAD/p15A vector. Plasmids pET28a(+) and pET22b(+) were purchased from Novagen. HotStart Taq Mastermix (Denville) was used for gene amplification from genomic or plasmid DNA. Phusion DNA polymerase (Finnizymes), Taq DNA ligase (MCLab), and T5 Exonuclease (Epicenter) were purchased separately and used to make the assembly master mix (AMM) used for cloning. ATP, (±)-α-lipoic acid, pyruvate, Coenzyme A, and NAD$^+$ were from Sigma.

Plasmid Construction.

The expression plasmids for the PHB enzymes were constructed from the pET28a plasmid backbone using the Nde1 and Sac1 cut sites to produce constructs with an N-terminal 6×His tag for purification. The genes encoding acetyl CoA acetyltransferase (phaA; YP_725941, the information associated with the accession number is incorporated herein by reference) and acetoacetyl-CoA reductase (phaB; YP_725942, the information associated with the accession number is incorporated herein by reference) were amplified and cloned from R. eutropha genomic DNA. The gene encoding polyhydroxybutyrate synthase (phaC; HE_610111, the information associated with the accession number is incorporated herein by reference) was synthesized and codon optimized for expression in an E. coli host before being subcloned into the pET28a expression vector. For the isoprene pathway, the constructs were the same as described in reference (Korman, T. P., Sahachartsiri, B., Li, D., Vinokur, J. M., Eisenberg, D. and Bowie, J. U. (2014), "A synthetic biochemistry system for the in vitro production of isoprene from glycolysis intermediates." Protein Science. doi: 10.1002/pro.2436).

E. coli BL21-Gold cells were used as the host strain for enzyme expression. All enzymes were expressed in Luria-Bertani (LB) media supplemented with 50 μg/mL kanamycin and were induced with 0.2 mM isopropyl-β-D-1-thiogalactopyranoside added to the culture at the end of log phase growth. The phaA, phaB, MVK, PMVK, and IspS were induced at 37° C. overnight and phaB, THL/HMGR, HMGS, and IDI were induced at 18° C. overnight. The phaC was induced at 25° C. for 5 hours before harvesting.

Enzyme Purification.

Cells from 0.5 L of culture were harvested by centrifugation and resuspended in 150 mM Tris pH 7.5, 100 mM NaCl. The cells were lysed on ice with sonication and the cell debris was removed by 12,000×g centrifugation at 4° C. The supernatant was then mixed with 5 mL nickel-nitrilotriacetic acid (NTA) agarose and after 30 minutes, the agarose slurry was loaded onto a gravity column and washed with five column volumes of 100 mM Tris pH 7.5, 100 mM NaCl, 15 mM imidazole. The enzyme was then eluted with 250 mM imidazole, 100 mM Tris pH 7.5. The resulting enzyme was dialyzed into 50 mM Tris pH 7.5, 50 mM NaCl and stored at 4° C.

Expression Vectors for PDH Subunits E1αβ, E2, and E3, and E. coli LplA.

The E1, E2, and E3 domains were all amplified separately from G. stearothermophilus genomic DNA (ATCC) using primers that contained 15-20 bp complementary to the gene and 15-20 bp complementary to the multiple cloning site in the vector where the gene would be placed. The genes encoding E1α and E1β were amplified together from G. stearothermophilus genomic DNA and cloned into pET28a (+) that had been digested with NcoI and XhoI. This created a tag-less construct for E1 expression under control of the T7 promoter where E1α translation uses the RBS from the pET28 vector while E1β uses the endogenous RBS from G. stearothermophilus. The E2 and E3 domains were amplified separately and cloned into pET22b(+) digested with NdeI and XhoI or pET28a(+) digested with NcoI and XhoI respectively to create tag-less E2 and E3 constructs. The E. coli lipoate protein ligase, LplA, was amplified from E. coli K12 genomic DNA and assembled into pBAD/p15A digested with XhoI and EcoRI to create 6×His-LplA.

Overexpression and Purification of G. sterothermophilus PDH Subunits and E. coli LplA.

All E. coli strains were grown at 37° C. in LB-media supplemented with appropriate antibiotic (100 μg/mL ampicillin, 50 μg/mL kanamycin, or 34 μg/mL chloramphenicol). For all constructs, 5 mL of overnight starter culture was used to inoculate 1 L of LB-media. Once the $OD_{600}$ reached 0.6, 0.3 mM IPTG (pET vectors) or 0.02% arabinose (pBAD/p15A) was added to induce protein expression. After 16 hours, cells were harvested, resuspended (4 mL/g wet cells) in 50 mM Tris-Cl pH 7.5, 0.1 M NaCl (Buffer A), lysed by sonication, and cell debris removed by centrifugation at 30,000×g for 20 min.

25 mL of the E. coli lysate containing 6×His-LplA was loaded onto a 3 mL Ni-NTA resin (Qiagen), washed with 25 mL Buffer A containing 10 mM imidazole, and eluted with 5 mL Buffer A containing 250 mM imidazole. Pure 6×His-LplA was then stored at 4° C. until use.

The individual domains of G. stearothermophilus PDH were partially purified from E. coli lysates by heat prior to modification and reconstitution of the PDH complex. E1αβ, E2, or E3 containing lysates were incubated at 65° C. for 35 minutes to heat denature E. coli proteins followed by centrifugation at 30,000×g for 20 min to pellet the precipitated proteins. Nearly all of the PDH domains remain in the supernatant. Next, the E2 domain was lipoated in the heated extract by the addition of 1 mM (±)-α-lipoic acid, 2 mM ATP, 3 mM $MgCl_2$, and 50 μg of purified 6×His-LplA. The lipoation reaction was then allowed to proceed with gentle mixing overnight at 25° C., yielding lipoated E2 (E2lip). After lipoation, E1αβ, E2lip, and E3 were mixed in a 3:1:3 molar ratio and incubated for at least 1 hour at 25° C. to form the active GsPDH complex. The GsPDH complex was then isolated by ultracentrifugation (Beckman) for 4 hours at 95,000×g. The resulting yellow pellet was resuspended in 20 mM Tris-Cl, pH 7.5 in 1/50 the starting volume and assayed for activity. SDS-PAGE analysis confirmed the presence of all 4 domains and indicated that the preparation was >90% pure. The reconstituted complex was stored at 4° C. until use.

Enzyme Activity and Optimization.

NoxE was assayed by monitoring the oxidation of NAD(P)H at 340 nm. The assay was carried out in 100 mM tris-HCl pH 7.5, 5 mM $MgCl_2$, 5 mM KCl, and 0.2 mM NAD(P)H.

WT and mutant PDH were assayed by monitoring the reduction of $NAD(P)^+$ at 340 nm. The assay was carried out in 50 mM Tris pH 7.5, 5 mM $MgCl_2$, 5 mM pyruvate, 1 mM CoA, and 0.5 mM of NAD (P)+.

PhaC was assayed by monitoring the absorbance of the hydrolysis of the thioester bond of the substrate 3HBCoA at 235 nm. The assay was carried out in 100 mM Tris pH 7.5, 5 mM $MgCl_2$ and 0.15 mM 3HBCoA.

Activity of isoprene pathway enzymes were measured as reported previously (Korman et al.). The amount of each enzyme in the reconstituted isoprene pathway described below is show in Table A.

TABLE A

List of the enzymes and activities used in the production of PHB or Isoprene from pyruvate.

| | Enzyme | Units/mg | mg added | Units added |
|---|---|---|---|---|
| 1 | $GsPDH^{NAD}$ | 0.082 ± 0.007 | 0.002/0.0013 | 0.00016/0.00011 |
| 1' | $GsPDH^{NADP}$ | 0.12 ± 0.008 | 0.076/0.0095 | 0.009/0.001 |
| 2 | NoxE | 0.35 ± 0.036 | 0.020/0.00625 | 0.007/0.0022 |
| 3 | PhaA | 76.2 ± 4.4 | 0.023 | 1.75 |
| 4 | PhaB | 6.1 ± 0.6 | 0.014 | 0.085 |
| 5 | PhaC | 142.7 | 0.032 | 4.57 |
| 6 | EfTHL-HMGR | 0.06 ± 0.002[a] | 0.003 | 0.00018 |
| 7 | EfHMGS[b] | 0.6 ± 0.01 | 0.041 | 0.025 |
| 8 | EfHMGR | 0.06 ± 0.002[a] | 0.023 | 0.0014 |
| 9 | ScMVK | 47.0 ± 0.9 | 0.008 | 0.38 |
| 10 | SsPMVK | 0.8 ± 0.02 | 0.029 | 0.023 |
| 11 | ScMDC | 4.0 ± .07 | 0.038 | 0.152 |
| 12 | EcIDI | 0.035[c] | 0.083 | 0.003 |
| 13 | PaIspS | 0.156[d] | 0.088 | 0.014 |

[a]Assayed in forward direction (synthesis) by coupling to MvaS and monitoring NADPH consumption Final PHB Reaction Conditions and Analysis.

The optimized self-sustaining reaction for the biotransformation of pyruvate to PHB was composed of 250 mM Tris pH 7.5, 5 mM MgCl, 5 mM KCl, 0.5 mM CoA, 0.1 mM $NAD^+$, 0.5 mM $NADP^+$, 50 mM pyruvate, 2 μg $PDH^{NA}DH$, 76 μg $PDH^{NADPH}$, 23 μg phaA, 14 μg phaB, and 32 μg phaC in a final reaction volume of 200 μL. The reactions were initiated with the addition of pyruvate, which was left out of the initial mixture. All PHB reactions were performed at room temperature. For testing the autoregulatory behavior of the purge valve, some enzyme concentrations were suboptimal: 5 μg phaA, 2.5 μg phaB, and 1.9 μg phaC.

To assay for PHB, the reactions were lyophilized and incubated with 1 mL chloroform, 0.45 mL methanol, and 0.05 mL $H_2SO_4$ to hydrolyze the polymer and generate methyl 3-hydroxybutyrate. The reactions were extracted with 0.5 ml water and 1 μL of the chloroform layer was applied to a 0.25 micron HP-Innowax column using a HP 5890 Series II gas chromatogram. The GC method used an injection temperature that was held at 35° C. for 5 minutes before it was increased to 275° C. over 40 minutes. The peak intensities were compared to an authentic standard to assess concentrations.

Isoprene Reaction Conditions and Analysis.

In vitro production of isoprene was performed as described previously (Korman et al.) with the following changes. 200 μL reactions were set up in 2 mL gas tight vials containing enzymes, 3 mM pyruvate, 15 mM ATP, 0.6 mM CoA, 0.2 mM NAD+, 0.4 mM NADP+(or 5 mM NADPH), 10 mM $MgCl_2$, 20 mM KCl, 0.1 mM thiamine pyrophosphate in 100 mM tris-Cl pH 8.5 and incubated at 32° C. for 18 hours. Isoprene production was monitored by direct sampling of 100 μL the headspace using a 100 μL gas-tight syringe. The headspace was analyzed by GC-FID (HP5980II) equipped with a GS-GasPro column (0.32 mm×30 m, Agilent). The amount of isoprene produced was quantified by comparison to a standard curve of various isoprene concentrations sampled in the same manner.

To implement the purge valve module, an $NADP^+$-utilizing PDH was needed. A mutant of E. coli PDH has been engineered to have $NADP^+$ specificity by introducing mutations into the E3 enzyme (EcE3). The E. coli PDH was, however, unstable. A mutant of the thermophilic G. stearothermophilus PDH was engineered that preferentially accepts $NADP^+$ with increased enzyme stability.

Figure 2:
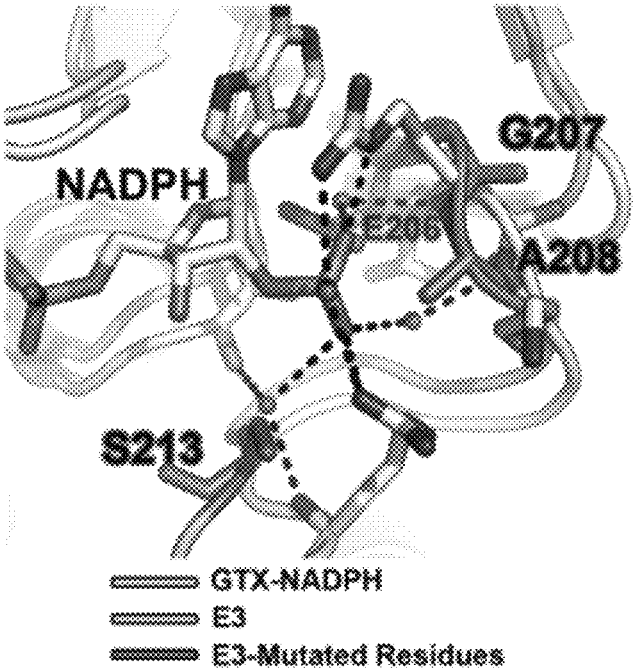
FIG. 2 shows the design of the $PDH^{NADPH}$ enzyme. The structures of the wild type G. stearothermophilus E3 subunit (E3, backbone trace) is shown overlaid on the structure of E. coli glutathione reductase (GTX-NADPH, gray backbone trace). The NADPH substrate from glutathione reductase is shown in stick representation, showing the placement of the phosphate moiety that needs to be accommodated. The residues changed to accept the phosphate (E206V, G207R, A208K, and S213R) are shown.

Similar to design of the E. coli PDH mutant, the G. stearothermophilus PDH mutant (SEQ ID NO:7) was designed by overlaying the known structure of the G. stearothermophilus E3 subunit (GsE3) with the known structure of the related E. coli glutathione reductase, which utilizes $NADP^+$. The structural superposition allowed for positioning the additional phosphate moiety in the active site of the GsE3, based on how it was placed in glutathione reductase (see FIG. 2). The side chain substitutions were then designed in GsE3 that might allow acceptance of the phosphate. Guidance was identified from a prior successful design of the EcE3 enzyme which shares 47% sequence identity with the GsE3. The mutations introduced into EcE3 were E206V, G207R, A208K, G209H and S213R (GsE3 numbering). After examining the changes in the context of the GsE3 structure, all were introduced but G209H, because it appeared that the new His side chain might create steric clashes with nearby K224 and N237 residues.

The kinetic properties of the engineered and wild-type enzymes reveal that the mutations alter specificity as desired. The kinetic parameters are listed in Table B. For the wild-type G. stearothermophilus enzyme ($GsPDH^{NADH}$), $k_{cat}$ is 11.2 times higher with $NAD^+$ than $NADP^+$ and $k_{cat}/K_m$ is 1150 times higher. For the engineered mutant ($GsPDH^{NADPH}$), $k_{cat}$ is 7.3 times higher with $NADP^+$ than NAD+ and $k_{cat}/K_m$ is 21 times higher. Thus, we were able to flip the specificity of the PDH enzyme.

TABLE B

List of the catalytic properties of the purge valve enzymes.

| Enzyme Name | Substrate | $K_m$ (mM) | $k_{cat}$ (μM/min/mg) | $k_{cat}/K_m$ |
|---|---|---|---|---|
| GsPDH – NAD+ | NAD+ | 0.013381 ± 0.00083 | 82.651 ± 0.66 | 6167.91 |
| | NADP+ | 1.381 ± 0.41 | 7.3954 ± 0.85 | 5.36 |
| | Pyruvate | 0.52736 ± 0.049 | 91.976 ± 1.9 | 174.40 |

TABLE B-continued

List of the catalytic properties of the purge valve enzymes.

| Enzyme Name | Substrate | $K_m$ (mM) | $k_{cat}$ (μM/min/mg) | $k_{cat}/K_m$ |
|---|---|---|---|---|
| GsPDH – NADP | NADP+ | 0.157 ± 0.013 | 117.75 ± 8.1 | 750.00 |
| | NAD+ | 0.45269 ± 0.178 | 16.104 ± 1.8 | 35.56 |
| | Pyruvate | 0.42328 ± 0.068 | 174.3 ± 2.7 | 411.76 |
| NoxE | NADH | 0.074925 ± 0.026 | 348.57 ± 36.5 | 4653.81 |
| | NADPH | 2.9515 ± 0.77 | 1.4009 ± 0.32 | 0.47 |

The $GsPDH^{NADH}$ and $GsPDH^{NADPH}$ enzymes (henceforth designated $PDH^{NADH}$ and $PDH^{NADPH}$) were much more stable than their E. coli counterparts. As shown in FIG. 7, the G stearothermophilus enzymes retained ~50% activity after one hour incubation at 67° C. whereas the E. coli PDH enzymes were completely inactivated at 50° C.

A second aspect of the purge valve design is the use of an NADH oxidase with high cofactor specificity. NoxE from L. lactis was selected as it is a water forming NADH oxidase so it doesn't generate any toxic products such as hydrogen peroxide. As shown in Table B, the $K_{cat}$ of NoxE is 248.8 times greater with NADH than NADPH and $k_{cat}/K_m$ is 9900 times greater.

The enzymes chosen for the various experiments are listed in Table C. In the initial tests only the wild type, $PDH^{NADH}$ complex and NoxE was used to generate Acetyl-CoA and NADPH was supplied exogenously. After optimizing enzyme ratios in this system, the mutant $PDH^{NADPH}$ was added to test in situ generation of NADPH. Finally, the amount of $PDH^{NADPH}$ was optimized, keeping the other enzymes fixed.

| | Enzyme | Name | Accession Number | Plasmid | Tag | Organism |
|---|---|---|---|---|---|---|
| | | | Purge Valve | | | |
| 1 | $PDH^{NADH}$ | Pyruvate Dehydrogenase Complex | | | | *G. stearothermophilus* |
| 1' | $PDH^{NADPH}$ | | | | | |
| 1a | E1a | Pyruvate Dehydrogenase Subunit a | P21873 (SEQ ID NO: 1) | pET28 | none | *G. stearothermophilus* |
| 1b | E1b | Pyruvate Dehydrogenase Subunit b | P21874 (SEQ ID NO: 2) | pET28 | none | *G. stearothermophilus* |
| 1c | E2 | Dihydrolipoamide Acetyltransferase | CAA37630 (SEQ ID NO: 3) | pET22 | none | *G. stearothermophilus* |
| 1d | $E3^{NADH}$ | Dihydrolipoamide Dehydrogenase | P11959 (SEQ ID NO: 5) | pET28 | none | *G. stearothermophilus* |
| 1'd | $E3^{NADPH}$ | Mutant Dihydrolipoamide Dehydrogenase | P11959 (SEQ ID NO: 7) | pET29 | none | *G. stearothermophilus* |
| 1e | LplA | Lipoate Protein Ligase | NP_418803 (SEQ ID NO: 8) | pBAD/p15A | N-His | *E. coli* |
| 2 | NoxE | NADH oxidase (H20 forming) | YP_007507681 (SEQ ID NO: 10) | pET22 | C-His | *L. lactis* |
| | | | PHB Pathway | | | |
| 3 | PhaA | Acetyl-CoA acetyltransferase | GJUJ-1435 (SEQ ID NO: 11) | pET28 | N-His | *R. eutropha* |
| 4 | PhaB | 3-hydroxybutryl-CoA reductase | GJUJ-1436 (SEQ ID NO: 12) | pET28 | N-His | *R. eutropha* |
| 5 | PhaC | Polyhydroxybutyrate synthase | G8BLJ2 (SEQ ID NO: 13) | pET28 | N-His | *C. necator* sp. S-6 |
| | | | Isoprene Pathway | | | |
| 6 | THL/HMGR | Thiolase/HMG-CoA Reductase fusion | WP_002357755 (SEQ ID NO: 14) | pET28 | N-His | *E. faecalis* |
| 7 | HMGS | HMG-CoA Synthase A110G Mutant | WP_010785222 (SEQ ID NO: 15) | pET28 | N-His | *E. faecalis* |
| 8 | HMGR | HMG-CoA Reductase | WP_002357755 (SEQ ID NO: 16) | pET28 | N-His | *E. faecalis* |
| 9 | MVK | mevalonate kinase | BAA24409 (SEQ ID NO: 17) | pET28 | N-His | *S. cerevisiae* |

-continued

| | Enzyme | Name | Accession Number | Plasmid | Tag | Organism |
|---|---|---|---|---|---|---|
| 10 | PMVK | phosphomevalonate kinase | NP_344303 (SEQ ID NO: 18) | pET28 | N-His | *S. solfataricus* |
| 11 | MDC | diphosphomevalonate decarboxylase | NP_014441 (SEQ ID NO: 19) | pET28 | N-His | *S. cerevisiae* |
| 12 | Idi | isopentenyl diphosphate isomerase | NP_417365 (SEQ ID NO: 20) | pET22 | C-His | *E. coli* |
| 13 | IspS | Isoprene Synthase | Q50L36 (SEQ ID NO: 21) | pET28 | N-His | *P. alba* |

The sequences associated with the foregoing accession numbers are incorporated herein by reference. The SEQ ID NOs set forth above provide the polypeptide sequences. The coding sequences are readily available to one of skill in the art.

Figure 3:
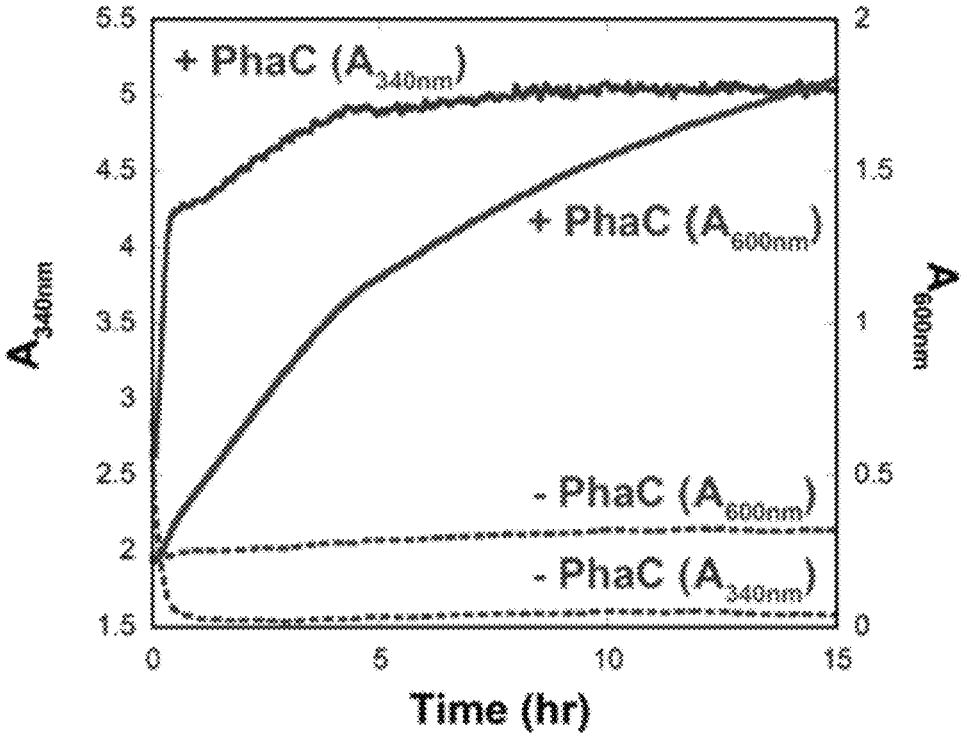
FIG. 3 shows the production of PHB using an optimized system. In this reaction the production of PHB is monitored by an increase $A_{600}$ caused by precipitation of the PHB granules. No increase is seen in the absence of the PHB polymerase, PhaC. The production of PHB is confirmed by a gas chromatography assay. The $A_{340}$ monitors the level of NADPH because no NADH is allowed to build up because of the presence of NoxE. The purge valve system maintains a high level of NADPH throughout the reaction.

The progress of the optimized pyruvate to PHB reaction is shown in FIG. 3 along with a control lacking the last enzyme, phaC. Both reactions had a $PDH^{NADPH}$:$PDH^{NADH}$ ratio of 40:1. At this ratio, the NADPH levels rise rapidly ($A_{340}$) and are maintained throughout the time course (NoxE rapidly oxidizes NADH so changes in $A_{340}$ reflect only changes in NADPH levels). At the same time, PHB granules are produced as monitored by $A_{600}$[36].

PHB production was assayed using a gas chromatography method and found that the optimized reaction produced 2.45±0.5 mg/mL of PHB from 50 mM pyruvate which represents nearly complete conversion (94±20%) of pyruvate to plastic. In the optimized system, 0.5 mM $NADP^+$ were initially used, so achieving 94% yield requires over 90 turnovers of the $NADP^+$ cofactor, indicating a high level of system sustainability.

The stability of the full system was assessed by mixing components together and then initiating the reaction at various time delays. The decrease in extent of the reaction is shown in FIG. 8. The extent of reaction remains 50% after two days.

Figure 4:
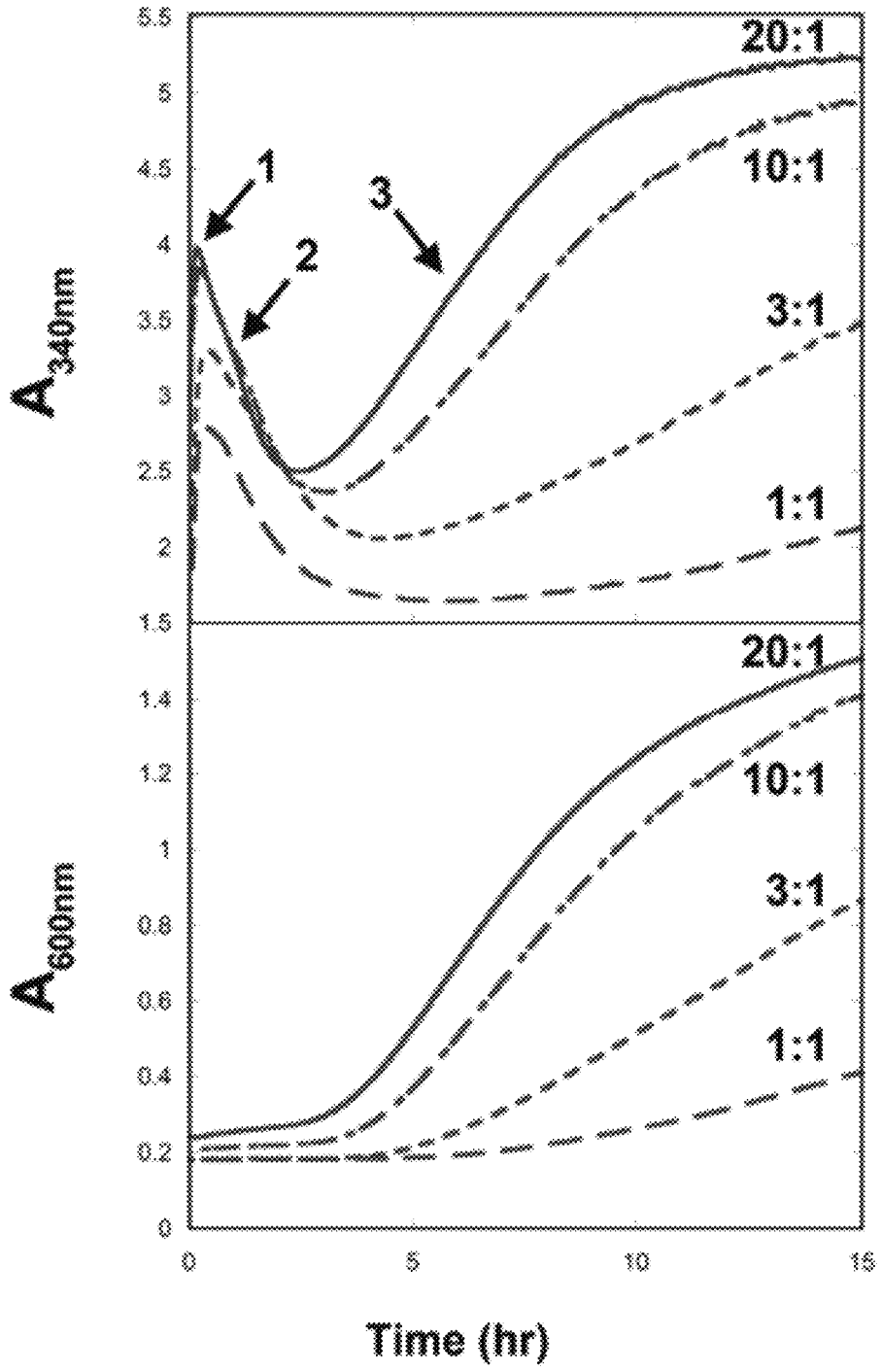
FIG. 4 shows a time course of pyruvate to PHB optimization reaction using sub-optimal ratios of $PDH^{NADPH}$ and $PDH^{NADH}$. The $A_{340}$ traces, monitoring NADPH levels fall into three distinct phases. A fast initial reduction of NADPH by the $PDH^{NADPH}$ is followed by a slow oxidation of NADPH by PhaB as the intermediate levels rise. As the reaction proceeds, the purge valve turns off and NADPH levels rise again. The evolution of the system coincides with the increase at $A_{600}$ which represents the precipitation of the PHB granules from solution.
Figure 5:
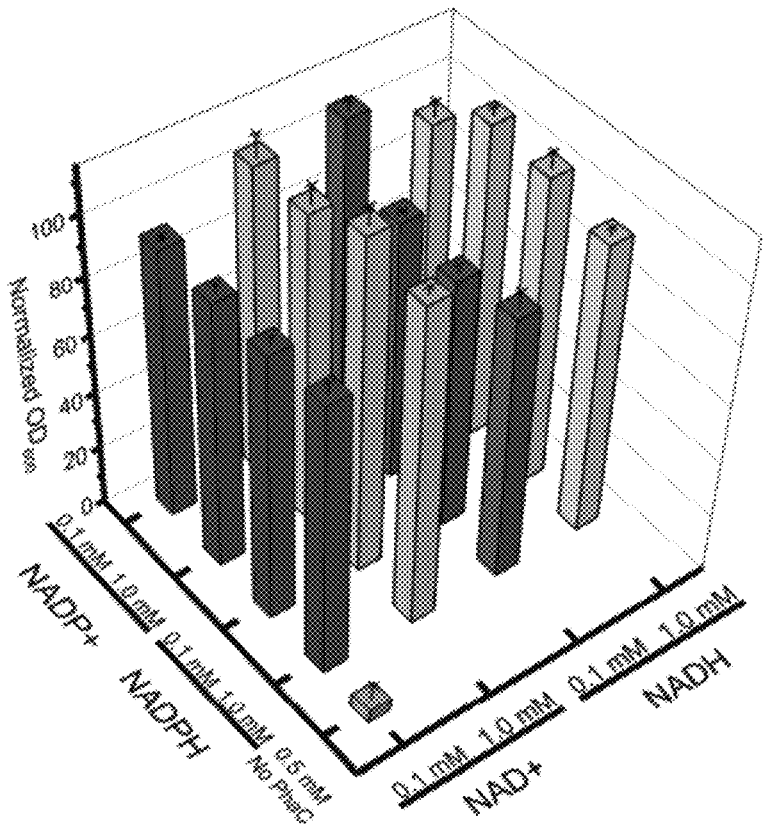
FIG. 5A-B shows the purge valve system is robust. (A) The graph shows relative yield of PHB upon starting with different amounts of each of the cofactors. The relative yields represent the ratio of the final $A_{600}$ for the reaction, relative to the final $A_{600}$ for the optimized reaction. All reactions show a relatively robust yield in comparison to the negative control lacking the final phaC enzyme (orange bar). The error bars reflect the standard deviation of three independent reactions. (B) Table of the numbers reflected in the graph in part A.

The regulatory behavior of the purge valve is better seen at sub-optimal enzyme concentrations and ratios of $PDH^{NADPH}$ to $PDH^{NADH}$ that slow down the response time. In the optimized assay (40:1 mole ratio of $PDH^{NADPH}$:$PDH^{NADH}$), a rapid rise in NADPH levels was observed, which was sustained throughout. In the non-optimal systems shown in FIG. 4, the purge valve cannot respond as rapidly to drops in NADPH concentrations so variations in NADPH levels were observed as the system develops. We still observe a rapid initial rise in NADPH levels, but as intermediates build up, the consumption starts to outstrip NADPH production. Eventually, the system compensates by generating higher levels of NADPH.

To test whether the system was robust to changes in cofactor levels, the initial cofactor concentrations were varied in the reactions and the yields of PHB were measured. Each reaction was constructed with combinations of $NAD^+$, NADH, $NADP^+$ or NADPH at either 0.1 mM or 1 mM and the production of PHB was monitored by the final OD at 600 nm. All of the reaction conditions were compared to the optimized reaction that produced nearly complete conversion of pyruvate to PHB and were within random variation. This result indicates that the purge valve can compensate readily for changes in cofactor concentrations and reduction states.

To test the versatility of the molecular purge valve and whether it can be applied as a general platform for the production of a diverse array Acetyl-CoA derived compounds the PDH purge valve was used to produce isoprene via the Acetyl-CoA dependent mevalonate pathway. Korman et al. previously described the in vitro production of isoprene from pyruvate, which required the use of exogenously added NADPH. Similar to the PHB pathway the mevalonate pathway has an inherently different carbon and cofactor stoichiometry. In particular, the mevalonate pathway requires 3 Acetyl-CoA and 2 NADPH for the production of isoprene (see FIG. 6A). Thus, system sustainability requires generation and regulation of NADPH levels.

Figure 6:
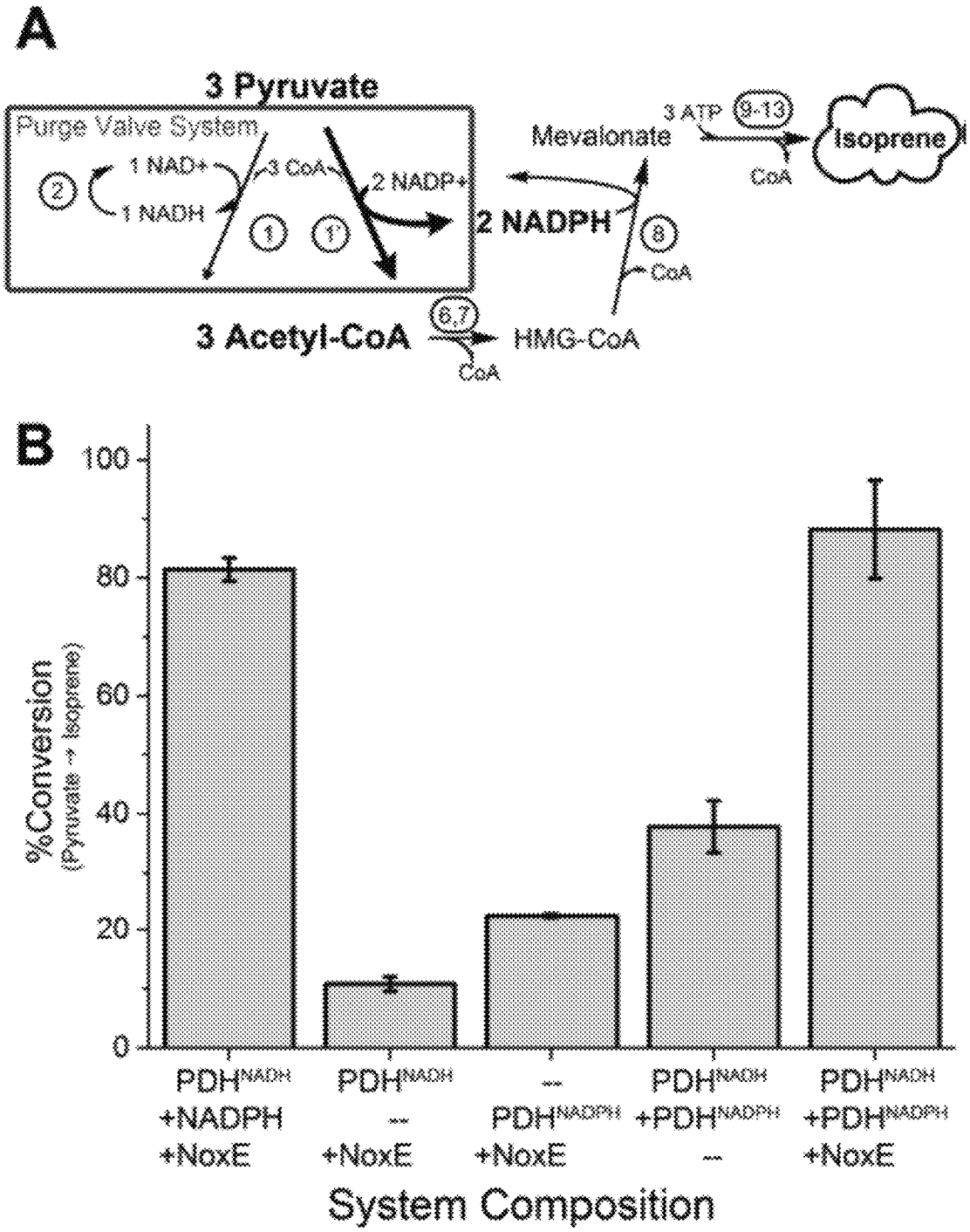
FIG. 6A-B shows employment of the purge valve for the production of isoprene. (A) The in vitro metabolic pathway for the conversion of pyruvate to isoprene. The purge valve highlighted in the box comprising the same enzymes/reactions as in FIG. 1A. In the mevalonate pathway, 3 Acetyl-CoA are used to make HMG-CoA (enzymes 6 and 7). HMG-CoA is reduced by HMGR (enzyme 8) with 2 NADPH to give mevalonate. 3 ATP are then used to convert mevalonate to isopentenyl pyrophosphate followed by production of isoprene (enzymes 9-12). (B) The graph shows the dependence of isoprene production on the purge valve.

Experiments were performed to test whether the purge valve system can replace exogenously added NADPH in the production of isoprene. As shown in FIG. 6B, the full purge valve system produces an 88.2±8.4% yield from 3 mM pyruvate. This yield is even higher than the 81.4±2.0% yield obtained if we add NADPH exogenously (FIG. 6B). If any of the purge valve components ($PDH^{NADPH}$, $PDH^{NADH}$ or NoxE) were left, yields are dramatically reduced. Thus, the purge valve system is transportable to other synthetic biochemistry systems.

A number of embodiments of the invention have been described. Nevertheless, it will be understood that various modifications may be made without departing from the spirit and scope of the invention. Accordingly, other embodiments are within the scope of the following claims.

SEQUENCE LISTING

```
Sequence total quantity: 21
SEQ ID NO: 1            moltype = AA  length = 369
FEATURE                 Location/Qualifiers
source                  1..369
                        mol_type = protein
                        organism = Geobacillus stearothermophilus
SEQUENCE: 1
MGVKTFQFPF AEQLEKVAEQ FPTFQILNEE GEVVNEEAMP ELSDEQLKEL MRRMVYTRIL  60
DQRSISLNRQ GRLGFYAPTA GQEASQIASH FALEKEDFIL PGYRDVPQII WHGLPLYQAF  120
LFSRGHFHGN QIPEGVNVLP PQIIIGAQYI QAAGVALGLK MRGKKAVAIT YTGDGGTSQG  180
DFYEGINFAG AFKAPAIFVV QNNRFAISTP VEKQTVAKTL AQKAVAAGIP GIQVDGMDPL  240
AVYAAVKAAR ERAINGEGPT LIETLCFRYG PHTMSGDDPT RYRSKELENE WAKKDPLVRF  300
```

```
RKFLEAKGLW SEEEENNVIE QAKEEIKEAI KKADETPKQK VTDLISIMFE ELPFNLKEQY  360
EIYKEKESK                                                          369

SEQ ID NO: 2            moltype = AA  length = 325
FEATURE                 Location/Qualifiers
source                  1..325
                        mol_type = protein
                        organism = Geobacillus stearothermophilus
SEQUENCE: 2
MAQMTMVQAI TDALRIELKN DPNVLIFGED VGVNGGVFRA TEGLQAEFGE DRVFDTPLAE  60
SGIGGLAIGL ALQGFRPVPE IQFFGFVYEV MDSICGQMAR IRYRTGGRYH MPITIRSPFG  120
GGVHTPELHS DSLEGLVAQQ PGLKVVIPST PYDAKGLLIS AIRDNDPVIF LEHLKLYRSF  180
RQEVPEGEYT IPIGKADIKR EGKDITIIAY GAMVHESLKA AAELEKEGIS AEVVDLRTVQ  240
PLDIETIIGS VEKTGRAIVV QEAQRQAGIA ANVVAEINER AILSLEAPVL RVAAPDTVYP  300
FAQAESVWLP NFKDVIETAK KVMNF                                        325

SEQ ID NO: 3            moltype = AA  length = 428
FEATURE                 Location/Qualifiers
source                  1..428
                        mol_type = protein
                        organism = Geobacillus stearothermophilus
SEQUENCE: 3
MAFEFKLPDI GEGIHEGEIV KWFVKPGDEV NEDDVLCEVQ NDKAVVEIPS PVKGKVLEIL  60
VPEGTVATVG QTLITLDAPG YENMTFKGQE QEEAKKEEKT ETVSKEEKVD AVAPNAPAAE  120
AEAGPNRRVI AMPSVRKYAR EKGVDIRLVQ GTGKNGRVLK EDIDAFLAGG AKPAPAAAEE  180
KAAPAAAKPA TTEGEFPETR EKMSGIRRAI AKAMVHSKHT APHVTLMDEA DVTKLVAHRK  240
KFKAIAAEKG IKLTFLPYVV KALVSALREY PVLNTSIDDE TEEIIQKHYY NIGIAADTDR  300
GLLVPVIKHA DRKPIFALAQ EINELAEKAR DGKLTPGEMK GASCTITNIG SAGGQWFTPV  360
INHPEVAILG IGRIAEKPIV RDGEIVAAPM LALSLSFDHR MIDGATAQKA LNHIKRLLSD  420
PELLLMEA                                                           428

SEQ ID NO: 4            moltype = DNA  length = 1413
FEATURE                 Location/Qualifiers
source                  1..1413
                        mol_type = other DNA
                        organism = Geobacillus stearothermophilus
SEQUENCE: 4
atggtagttg gcgattttgc aattgaaacg gaaacgcttg tcgtcggcgc cggtcctggc  60
gggtatgtcg ccgccatccg cgccgcgcag ctcggacaaa aagtgacgat tgtggaaaag  120
ggcaatttag gcggcgtctg cttaaatgtt ggctgcatcc cgtcaaaggc gctgatctcc  180
gcaagccatc gctatgagca ggcgaagcat tccgaagaaa tgggcattaa ggcggagaac  240
gtcaccatcg attttgccaa agtgcaagaa tggaaagcaa gcgtcgtgaa aaaattaacg  300
ggcggcgtcg aagggctgtt aaaaggaaac aaagtagaga tcgtcaaagg ggaagcgtat  360
tttgtcgacg ccaatacggt gcgtgtcgtc aacggcgaca gcgcgcagac gtatacgttc  420
aaaaacgcga ttatcgccac cggctcgcgc ccgattgagc tgccgaactt caagttttcc  480
aaccgcattc ttgactcgac gggagctctc aaccttgggg aagtgccgaa atcgctcgtg  540
gtcatcggcg gcggctatat tggcatcgaa ctcggtacgg cttacgccaa ctttgggacg  600
aaagtgacca ttttagaagg agccggcgaa attttgtccg gttttgagaa gcaaatggct  660
gccatcatca agaagcgcct gaagaaaaaa ggcgttgaag tcgtgacgaa cgcattggcg  720
aaaggggccg aagaacgcga agacggcgtc acggtcacgt atgaggcgaa tggtgaaacg  780
aaaacgattg acgccgacta tgtgctcgtc accgtcggcc gccgtccgaa tacagatgaa  840
cttggtcttg aacaaatcgg catcaaaatg acgaaccgcg gcttgattga agtggaccaa  900
caatgccgga caagcgtgcc gaacattttt gcgatcggcg acatcgttcc aggtccggcg  960
ctcgcccata aagcgtcgta tgaaggaaaa gtggctgcgg aagctatcgc cggccatccg  1020
tcggcagtcg attacgtggc cattccagct gttgtcttct ccgatccgga atgcgcgtcg  1080
gtcggctatt ttgagcagca ggcgaaagac gagggcattg acgtcattgc cgcgaaattc  1140
ccgtttgctg ccaacggccg cgccttggcg ctgaacgata cggacggctt cttgaagctc  1200
gttgtccgca aagaggacgg cgtcatcatt ggtgcgcaaa tcatcggtcc aaatgcttct  1260
gacatgatcg ccgagcttgg gctcgccatt gaagccggca tgacggcgga agacatcgct  1320
ttgacgatcc atgcccatcc gacgcttggc gaaatcgcca tggaagcggc ggaagtggcg  1380
cttggcacac cgattcatat cattacgaag taa                               1413

SEQ ID NO: 5            moltype = AA  length = 470
FEATURE                 Location/Qualifiers
source                  1..470
                        mol_type = protein
                        organism = Geobacillus stearothermophilus
SEQUENCE: 5
MVVGDFAIET ETLVVGAGPG GYVAAIRAAQ LGQKVTIVEK GNLGGVCLNV GCIPSKALIS  60
ASHRYEQAKH SEEMGIKAEN VTIDFAKVQE WKASVVKKLT GGVEGLLKGN KVEIVKGEAY  120
FVDANTVRVV NGDSAQTYTF KNAIIATGSR PIELPNFKFS NRILDSTGAL NLGEVPKSLV  180
VIGGGYIGIE LGTAYANFGT KVTILEGAGE ILSGFEKQMA AIIKKRLKKK GVEVVTNALA  240
KGAEEREDGV TVTYEANGET KTIDADYVLV TVGRRPNTDE LGLEQIGIKM TNRGLIEVDQ  300
QCRTSVPNIF AIGDIVPGPA LAHKASYEGK VAAEAIAGHP SAVDYVAIPA VVFSDPECAS  360
VGYFEQQAKD EGIDVIAAKF PFAANGRALA LNDTDGFLKL VVRKEDGVII GAQIIGPNAS  420
DMIAELGLAI EAGMTAEDIA LTIHAHPTLG EIAMEAAEVA LGTPIHIITK             470

SEQ ID NO: 6            moltype = DNA  length = 1413
FEATURE                 Location/Qualifiers
```

```
misc_feature            1..1413
                        note = Mutated Dihydrolipoamide dehydrogenase from
                         Geobacillus stearothermophilus
source                  1..1413
                        mol_type = other DNA
                        organism = synthetic construct
SEQUENCE: 6
atggtagttg gcgattttgc aattgaaacg gaaacgcttg tcgtcggcgc cggtcctggc  60
gggtatgtcg ccgccatccg cgccgcgcag ctcggacaaa aagtgacgat tgtggaaaag  120
ggcaatttag gcggcgtctg cttaaatgtt ggctgcatcc cgtcaaaggc gctgatctcc  180
gcaagccatc gctatgagca ggcgaagcat tccgaagaaa tgggcattaa ggcggagaac  240
gtcaccatcg attttgccaa agtgcaagaa tggaaagcaa gcgtcgtgaa aaaattaacg  300
ggcggcgtcg aagggctgtt aaaaggaaac aaagtagaga tcgtcaaagg ggaagcgtat  360
tttgtcgacg ccaatacggt gcgtgtcgtc aacggcgaca gcgcgcagac gtatacgttc  420
aaaaacgcga ttatcgccac cggctcgcgc ccgattgagc tgccgaactt caagttttcc  480
aaccgcattc ttgactcgac gggagctctc aaccttgggg aagtgccgaa atcgctcgtg  540
gtcatcggcg gcggctatat tgcgatcgaa ctcgcgacgg cttacgccaa ctttgggacg  600
aaagtgacca ttttagtgcg taaaggcgaa attttgcgtg gttttgagaa gcaaatggct  660
gccatcatca agaagcgcct gaagaaaaaa ggcgttgaag tcgtgacgaa cgcattggcg  720
aaaggggccg aagaacgcga agacggcgtc acggtcacgt atgaggcgaa tggtgaaacg  780
aaaacgattg acgccgacta tgtgctcgtc accgtcggcc gccgtccgaa tacagatgaa  840
cttggtcttg aacaaatcgg catcaaaatg acgaaccgcg gcttgattga agtggaccaa  900
caatgccgga caagcgtgcc gaacattttt gcgatcggcg acatcgttcc aggtccggcg  960
ctcgcccata aagcgtcgta tgaaggaaaa gtggctgcgg aagctatcgc cggccatccg  1020
tcggcagtcg attacgtggc cattccagct gttgtcttct ccgatccgga atgcgcgtcg  1080
gtcggctatt ttgagcagca ggcgaaagac gagggcattg acgtcattgc cgcgaaattc  1140
ccgtttgctg ccaacggccg cgccttggcg ctgaacgata cggacggctt cttgaagctc  1200
gttgtccgca aagaggacgg cgtcatcatt ggtgcgcaaa tcatcggtcc aaatgcttct  1260
gacatgatcg ccgagcttgg gctcgccatt gaagccggca tgacggcgga agacatcgct  1320
ttgacgatcc atgcccatcc gacgcttggc gaaatcgcca tggaagcggc ggaagtggcg  1380
cttggcacac cgattcatat cattacgaag taa                               1413

SEQ ID NO: 7            moltype = AA  length = 470
FEATURE                 Location/Qualifiers
source                  1..470
                        mol_type = protein
                        organism = synthetic construct
SEQUENCE: 7
MVVGDFAIET ETLVVGAGPG GYVAAIRAAQ LGQKVTIVEK GNLGGVCLNV GCIPSKALIS  60
ASHRYEQAKH SEEMGIKAEN VTIDFAKVQE WKASVVKKLT GGVEGLLKGN KVEIVKGEAY  120
FVDANTVRVV NGDSAQTYTF KNAIIATGSR PIELPNFKFS NRILDSTGAL NLGEVPKSLV  180
VIGGGYIAIE LATAYANFGT KVTILVRKGE ILRGFEKQMA AIIKKRLKKK GVEVVTNALA  240
KGAEEREDGV TVTYEANGET KTIDADYVLV TVGRRPNTDE LGLEQIGIKM TNRGLIEVDQ  300
QCRTSVPNIF AIGDIVPGPA LAHKASYEGK VAAEAIAGHP SAVDYVAIPA VVFSDPECAS  360
VGYFEQQAKD EGIDVIAAKF PFAANGRALA LNDTDGFLKL VVRKEDGVII GAQIIGPNAS  420
DMIAELGLAI EAGMTAEDIA LTIHAHPTLG EIAMEAAEVA LGTPIHIITK             470

SEQ ID NO: 8            moltype = AA  length = 338
FEATURE                 Location/Qualifiers
source                  1..338
                        mol_type = protein
                        organism = Escherichia coli
SEQUENCE: 8
MSTLRLLISD SYDPWFNLAV EECIFRQMPA TQRVLFLWRN ADTVVIGRAQ NPWKECNTRR  60
MEEDNVRLAR RSSGGGAVFH DLGNTCFTFM AGKPEYDKTI STSIVLNALN ALGVSAEASG  120
RNDLVVKTVE GDRKVSGSAY RETKDRGFHH GTLLLNADLS RLANYLNPDK KKLAAKGITS  180
VRSRVTNLTE LLPGITHEQV CEAITEAFFA HYGERVEAEI ISPNKTPDLP NFAETFARQS  240
SWEWNFGQAP AFSHLLDERF TWGGVELHFD VEKGHITRAQ VFTDSLNPAP LEALAGRLQG  300
CLYRADMLQQ ECEALLVDFP EQEKELRELS AWMAGAVR                          338

SEQ ID NO: 9            moltype = DNA  length = 1341
FEATURE                 Location/Qualifiers
source                  1..1341
                        mol_type = other DNA
                        organism = Lactococcus lactis
SEQUENCE: 9
atgaaaatcg tagttatcgg tacgaaccac gcaggcattg ctacagcaaa tacattaatt  60
gatcgatatc caggccatga gattgttatg attgaccgta acagtaatat gagttacttg  120
gggtgtggga cagctatttg ggtcggaaga caaattgaaa aaccagatga gctgttttat  180
gccaaagcag aagattttga aaaaaaggga gtaaagatat taacagaaac agaagtttca  240
gaaattgact ttactaataa aatgatttat gccaagtcaa aaactggaga aaagattaca  300
gaaagttatg ataaactcgt tctggcaaca ggttcacgtc caattattcc taacttgcca  360
ggaaaagatc ttaaaggcat tcatttttta aaactttttc aagaagggca agccattgac  420
gaagagtttg ctaagaatga tgtgaaacgg attgctgtga ttggtgctgg ttatattggg  480
acagaaattg ctgaagctgc caaacgtcgt ggaaaagaag tcctactttt tgatgcagaa  540
agtacttcac ttgcttcata ttatgatgaa gagtttgcta aagggatgga tgaaaatctt  600
gcccaacatg gaattgaact ccattttggg gaattagctc aagagtttaa ggcaaatgaa  660
aaaggtcatg tatcacagat tgtaactaat aaatcaactt atgatgttga cctcgttatt  720
aattgtattg gctttacagc caatagtgca ttggctggtg aacatttaga aacctttaaa  780
```

```
aatggagcaa tcaaagtgga taaacatcaa caaagtagtg acccagatgt ttctgctgta  840
ggagatgttg ccacaatcta ttctaatgct ttacaagact tcacctacat tgcccttgcc  900
tcaaacgctg ttcgctcagg gattgttgct ggtcataata ttggaggaaa atcaatagag  960
tctgttggtg tacaaggttc taatggaatc tctatttttg gttacaatat gacttctacg  1020
ggcttgtcgg ttaaagctgc gaaaaaaatc ggcctagaag tttcatttag tgattttgaa  1080
gataagcaaa aagcatggtt ccttcatgaa aataatgata gtgtgaaaat tcgtatcgtt  1140
tatgaaacaa aaaatcgcag aattattggt gctcaacttg ctagcaagag tgaaataatt  1200
gcaggaaata ttaatatgtt tagtttagct attcaagaaa agaaaacgat tgatgaatta  1260
gccttacttg atttattctt cttaccacac ttcaatagtc catataatta catgactgtt  1320
gcagctttaa atgcaaaata a                                            1341

SEQ ID NO: 10          moltype = AA  length = 446
FEATURE                Location/Qualifiers
source                 1..446
                       mol_type = protein
                       organism = Lactococcus lactis
SEQUENCE: 10
MKIVVIGTNH AGIATANTLI DRYPGHEIVM IDRNSNMSYL GCGTAIWVGR QIEKPDELFY  60
AKAEDFEKKG VKILTETEVS EIDFTNKMIY AKSKTGEKIT ESYDKLVLAT GSRPIIPNLP  120
GKDLKGIHFL KLFQEGQAID EEFAKNDVKR IAVIGAGYIG TEIAEAAKRR GKEVLLFDAE  180
STSLASYYDE EFAKGMDENL AQHGIELHFG ELAQEFKANE KGHVSQIVTN KSTYDVDLVI  240
NCIGFTANSA LAGEHLETFK NGAIKVDKHQ QSSDPDVSAV GDVATIYSNA LQDFTYIALA  300
SNAVRSGIVA GHNIGGKSIE SVGVQGSNGI SIFGYNMTST GLSVKAAKKI GLEVSFSDFE  360
DKQKAWFLHE NNDSVKIRIV YETKNRRIIG AQLASKSEII AGNINMFSLA IQEKKTIDEL  420
ALLDLFFLPH FNSPYNYMTV AALNAK                                       446

SEQ ID NO: 11          moltype = AA  length = 393
FEATURE                Location/Qualifiers
source                 1..393
                       mol_type = protein
                       organism = Ralstonia eutropha
SEQUENCE: 11
MTDVVIVSAA RTAVGKFGGS LAKIPAPELG AVVIKAALER AGVKPEQVSE VIMGQVLTAG  60
SGQNPARQAA IKAGLPAMVP AMTINKVCGS GLKAVMLAAN AIMAGDAEIV VAGGQENMSA  120
APHVLPGSRD GFRMGDAKLV DTMIVDGLWD VYNQYHMGIT AENVAKEYGI TREAQDEFAV  180
GSQNKAEAAQ KAGKFDEEIV PVLIPQRKGD PVAFKTDEFV RQGATLDSMS GLKPAFDKAG  240
TVTAANASGL NDGAAAVVVM SAAKAKELGL TPLATIKSYA NAGVDPKVMG MGPVPASKRA  300
LSRAEWTPQD LDLMEINEAF AAQALAVHQQ MGWDTSKVNV NGGAIAIGHP IGASGCRILV  360
TLLHEMKRRD AKKGLASLCI GGGMGVALAV ERK                               393

SEQ ID NO: 12          moltype = AA  length = 246
FEATURE                Location/Qualifiers
source                 1..246
                       mol_type = protein
                       organism = Ralstonia eutropha
SEQUENCE: 12
MTQRIAYVTG GMGGIGTAIC QRLAKDGFRV VAGCGPNSPR REKWLEQQKA LGFDFIASEG  60
NVADWDSTKT AFDKVKSEVG EVDVLINNAG ITRDVVFRKM TRADWDAVID TNLTSLFNVT  120
KQVIDGMADR GWGRIVNISS VNGQKGQFGQ TNYSTAKAGL HGFTMALAQE VATKGVTVNT  180
VSPGYIATDM VKAIRQDVLD KIVATIPVKR LGLPEEIASI CAWLSSEESG FSTGADFSLN  240
GGLHMG                                                             246

SEQ ID NO: 13          moltype = AA  length = 605
FEATURE                Location/Qualifiers
source                 1..605
                       mol_type = protein
                       organism = Cupriavidus necator
SEQUENCE: 13
MATGKGAAAS GQEEKTTPFS STPGPFDPAT WLEWSRQAQA NGRAAGGMPG ADAFAALGAF  60
PGGAFPGAGF PGTAFPGIKI APAQLAEIQQ RFMQGFTDLW RAMAAGDQQQ VQLTDRRFAG  120
DAWRSNAPYR YAAAFYLLTA RAMSEMADAV EADAKTRQRI RFAVTQWVDA MSPANFLATN  180
PEAQRRLIES NGESLRAGLR NMLEDLTRGK ISQTDESAFE VGRNVAVTEG AVVYENEYFQ  240
LLQYKPLTAK VHARPLLMVP PCINKYYILD LQPESSLVRH IVEQGHTVFL VSWRNPDASM  300
AARTWDDYIE HGAIRAIEVA RAISGQPRIN VLGFCVGGTI VSTALAVMAG RGERPAQSLT  360
LLTTLLDFSD TGVLDVFVDE AHVQLREATL GGAAGAPCAL LRGIELANTF SFLRPNDLVW  420
NYVVDNYLKG NTPVPFDLLF WNGDATNLPG PWYCWYLRHT YLQDELKVPG KLTVCGVPVD  480
LGKIDVPTYL YGSREDHIVP WTAAYASTRL LSNDLRFVLG ASGHIAGVIN PPAKNKRSHW  540
LNEDLPDSPN DWLAGATEAP GSWWPDWFAW LGKHAGAKKA APTQYGSRDY PAIEPAPGRY  600
VKAKA                                                              605

SEQ ID NO: 14          moltype = AA  length = 803
FEATURE                Location/Qualifiers
source                 1..803
                       mol_type = protein
                       organism = Enterococcus faecalis
SEQUENCE: 14
MKTVVIIDAL RTPIGKYKGS LSQVSAVDLG THVTTQLLKR HSTISEEIDQ VIFGNVLQAG  60
NGQNPARQIA INSGLSHEIP AMTVNEVCGS GMKAVILAKQ LIQLGEAEVL IAGGIENMSQ  120
APKLQRFNYE TESYDAPFSS MMYDGLTDAF SGQAMGLTAE NVAEKYHVTR EEQDQFSVHS  180
```

```
QLKAAQAQAE GIFADEIAPL EVSGTLVEKD EGIRPNSSVE KLGTLKTVFK EDGTVTAGNA  240
STINDGASAL IIASQEYAEA HGLPYLAIIR DSVEVGIDPA YMGISPIKAI QKLLARNQLT  300
TEEIDLYEIN EAFAATSIVV QRELALPEEK VNIYGGGISL GHAIGATGAR LLTSLSYQLN  360
QKEKKYGVAS LCIGGGLGLA MLLERPQQKK NSRFYQMSPE ERLASLLNEG QISADTKKEF  420
ENTALSSQIA NHMIENQISE TEVPMGVGLH LTVDETDYLV PMATEEPSVI AALSNGAKIA  480
QGFKTVNQQR LMRGQIVFYD VADAESLIDE LQVRETEIFQ QAELSYPSIV KRGGGLRDLQ  540
YRAFDESFVS VDFLVDVKDA MGANIVNAML EGVAELFREW FAEQKILFSI LSNYATESVV  600
TMKTAIPVSR LSKGSNGREI AEKIVLASRY ASLDPYRAVT HNKGIMNGIE AVVLATGNDT  660
RAVSASCHAF AVKEGRYQGL TSWTLDGEQL IGEISVPLAL ATVGGATKVL PKSQAAADLL  720
AVTDAKELSR VVAAVGLAQN LAALRALVSE GIQKGHMALQ ARSLAMTVGA TGKEVEAVAQ  780
QLKRQKTMNQ DRALAILNDL RKQ                                          803

SEQ ID NO: 15          moltype = AA  length = 383
FEATURE                Location/Qualifiers
REGION                 1..383
                       note = Mutant Hydroxymethylglutaryl-CoA synthase from
                        Enterococcus faecalis
source                 1..383
                       mol_type = protein
                       organism = synthetic construct
SEQUENCE: 15
MTIGIDKISF FVPPYYIDMT ALAEARNVDP GKFHIGIGQD QMAVNPISQD IVTFAANAAE  60
AILTKEDKEA IDMVIVGTES SIDESKAAAV VLHRLMGIQP FARSFEIKEG CYGATAGLQL  120
AKNHVALHPD KKVLVVAADI AKYGLNSGGE PTQGAGAVAM LVASEPRILA LKEDNVMLTQ  180
DIYDFWRPTG HPYPMVDGPL SNETYIQSFA QVWDEHKKRT GLDFADYDAL AFHIPYTKMG  240
KKALLAKISD QTEAEQERIL ARYEESIIYS RRVGNLYTSS LYLGLISLLE NATTLTAGNQ  300
IGLFSYGSGA VAEFFTGELV AGYQNHLQKE THLALLDNRT ELSIAEYEAM FAETLDTDID  360
QTLEDELKYS ISAINNTVRS YRN                                          383

SEQ ID NO: 16          moltype = AA  length = 803
FEATURE                Location/Qualifiers
source                 1..803
                       mol_type = protein
                       organism = Enterococcus faecalis
SEQUENCE: 16
MKTVVIIDAL RTPIGKYKGS LSQVSAVDLG THVTTQLLKR HSTISEEIDQ VIFGNVLQAG  60
NGQNPARQIA INSGLSHEIP AMTVNEVCGS GMKAVILAKQ LIQLGEAEVL IAGGIENMSQ  120
APKLQRFNYE TESYDAPFSS MMYDGLTDAF SGQAMGLTAE NVAEKYHVTR EEQDQFSVHS  180
QLKAAQAQAE GIFADEIAPL EVSGTLVEKD EGIRPNSSVE KLGTLKTVFK EDGTVTAGNA  240
STINDGASAL IIASQEYAEA HGLPYLAIIR DSVEVGIDPA YMGISPIKAI QKLLARNQLT  300
TEEIDLYEIN EAFAATSIVV QRELALPEEK VNIYGGGISL GHAIGATGAR LLTSLSYQLN  360
QKEKKYGVAS LCIGGGLGLA MLLERPQQKK NSRFYQMSPE ERLASLLNEG QISADTKKEF  420
ENTALSSQIA NHMIENQISE TEVPMGVGLH LTVDETDYLV PMATEEPSVI AALSNGAKIA  480
QGFKTVNQQR LMRGQIVFYD VADAESLIDE LQVRETEIFQ QAELSYPSIV KRGGGLRDLQ  540
YRAFDESFVS VDFLVDVKDA MGANIVNAML EGVAELFREW FAEQKILFSI LSNYATESVV  600
TMKTAIPVSR LSKGSNGREI AEKIVLASRY ASLDPYRAVT HNKGIMNGIE AVVLATGNDT  660
RAVSASCHAF AVKEGRYQGL TSWTLDGEQL IGEISVPLAL ATVGGATKVL PKSQAAADLL  720
AVTDAKELSR VVAAVGLAQN LAALRALVSE GIQKGHMALQ ARSLAMTVGA TGKEVEAVAQ  780
QLKRQKTMNQ DRALAILNDL RKQ                                          803

SEQ ID NO: 17          moltype = AA  length = 246
FEATURE                Location/Qualifiers
source                 1..246
                       mol_type = protein
                       organism = Saccharomyces cerevisiae
SEQUENCE: 17
MSLPFLTSAP GKVIIFGEHS AVYNKPAVAA SVSALRTYLL ISESSAPDTI ELDFPDISFN  60
HKWSINDFNA ITEDQVNSQK LAKAQQATDG LSQELVSLLD PLLAQLSESF HYHAAFCFLY  120
MFVCLCPHAK NIKFSLKSTL PIGAGLGSSA SISVSLALAM AYLGGLIGSN DLEKLSENDK  180
HIVNQWAFIG EKCIHGTPSG IDNAVATYGN ALLFEKDSHN GTINTNNFKF LDDFPAIPMI  240
LTYTRI                                                             246

SEQ ID NO: 18          moltype = AA  length = 323
FEATURE                Location/Qualifiers
source                 1..323
                       mol_type = protein
                       organism = Sulfolobus solfataricus
SEQUENCE: 18
MIKVSAPGKI LWIGSYSVVF GGISHVIAVN KRVSCSLREI KEKDSLIFHT SYGHFKNSGN  60
ELINSVLDTF RERLSQLPQG YEIDLYNDKE FIIDGKKTGL GSSSAATVSL TACLYYAIHG  120
KLDLFEIHKL AQIANYKRQK GIGSGFDIAS AVFGSIVYKR FTDLDKMDFY FEKLNLGNYD  180
MMLGFTGKSS ETVGLVRKFV EKSNLDDFKE IMRLIDEENY MAIKLIKLNK LDEAVEHIKL  240
GRKYLNYIAE RIVGVKLVSK MEEELIKIAE EEGALVALSP GAGGGDSIFA LGNDLNRVRE  300
AWSKRGIFII DVKEDEGLRL ESN                                          323

SEQ ID NO: 19          moltype = AA  length = 396
FEATURE                Location/Qualifiers
source                 1..396
                       mol_type = protein
```

-continued

```
                        organism = Saccharomyces cerevisiae
SEQUENCE: 19
MTVYTASVTA PVNIATLKYW GKRDTKLNLP TNSSISVTLS QDDLRTLTSA ATAPEFERDT  60
LWLNGEPHSI DNERTQNCLR DLRQLRKEME SKDASLPTLS QWKLHIVSEN NFPTAAGLAS  120
SAAGFAALVS AIAKLYQLPQ STSEISRIAR KGSGSACRSL FGGYVAWEMG KAEDGHDSMA  180
VQIADSSDWP QMKACVLVVS DIKKDVSSTQ GMQLTVATSE LFKERIEHVV PKRFEVMRKA  240
IVEKDFATFA KETMMDSNSF HATCLDSFPP IFYMNDTSKR IISWCHTINQ FYGETIVAYT  300
FDAGPNAVLY YLAENESKLF AFIYKLFGSV PGWDKKFTTE QLEAFNHQFE SSNFTARELD  360
LELQKDVARV ILTQVGSGPQ ETNESLIDAK TGLPKE                            396

SEQ ID NO: 20           moltype = AA  length = 182
FEATURE                 Location/Qualifiers
source                  1..182
                        mol_type = protein
                        organism = Escherichia coli
SEQUENCE: 20
MQTEHVILLN AQGVPTGTLE KYAAHTADTR LHLAFSSWLF NAKGQLLVTR RALSKKAWPG  60
VWTNSVCGHP QLGESNEDAV IRRCRYELGV EITPPESIYP DFRYRATDPS GIVENEVCPV  120
FAARTTSALQ INDDEVMDYQ WCDLADVLHG IDATPWAFSP WMVMQATNRE ARKRLSAFTQ  180
LK                                                                 182

SEQ ID NO: 21           moltype = AA  length = 595
FEATURE                 Location/Qualifiers
source                  1..595
                        mol_type = protein
                        organism = Populus alba
SEQUENCE: 21
MATELLCLHR PISLTHKLFR NPLPKVIQAT PLTLKLRCSV STENVSFTET ETEARRSANY  60
EPNSWDYDYL LSSDTDESIE VYKDKAKKLE AEVRREINNE KAEFLTLLEL IDNVQRLGLG  120
YRFESDIRGA LDRFVSSGGF DAVTKTSLHG TALSFRLLRQ HGFEVSQEAF SGFKDQNGNF  180
LENLKEDIKA ILSLYEASFL ALEGENILDE AKVFAISHLK ELSEEKIGKE LAEQVNHALE  240
LPLHRRTQRL EAVWSIEAYR KKEDANQVLL ELAILDYNMI QSVYQRDLRE TSRWWRRVGL  300
ATKLHFARDR LIESFYWAVG VAFEPQYSDC RNSVAKMFSF VTIIDDIYDV YGTLDELELF  360
TDAVERWDVN AINDLPDYMK LCFLALYNTI NEIAYDNLKD KGENILPYLT KAWADLCNAF  420
LQEAKWLYNK STPTFDDYFG NAWKSSSGPL QLVFAYFAVV QNIKKEEIEN LQKYHDTISR  480
PSHIFRLCND LASASAEIAR GETANSVSCY MRTKGISEEL ATESVMNLID ETWKKMNKEK  540
LGGSLFAKPF VETAINLARQ SHCTYHNGDA HTSPDELTRK RVLSVITEPI LPFER       595
```

What is claimed is:

1. A recombinant, artificial or engineered metabolic pathway comprising a plurality of enzymatic steps that converts a substrate to a product, wherein the pathway produces an unbalanced production of [a cofactor] *cofactors*, said pathway comprising:

a first cofactor-dependent enzyme that is capable of converting a first substrate to a second substrate, said *first cofactor-dependent* enzyme producing the unbalanced production of a *first* cofactor; and a second cofactor-dependent enzyme [comprising] *that uses a second cofactor different from the first cofactor-dependent enzyme and that converts the first substrate to the second substrate and wherein said second cofactor-dependent enzyme produces an unbalanced production of the second cofactor, and wherein the pathway comprises* an NADH or an NADPH oxidase that recycles [the] *an NADH or NADPH* cofactor.

2. The recombinant, artificial or engineered pathway of claim 1, wherein the *first and second* [co-factor is an] *co-factors are* oxidizing/reducing [co-factor] *co-factors*.

3. The recombinant, artificial or engineered pathway of claim 2, wherein the oxidizing/reducing [co-factor is] *co-factors are* selected from the group consisting of $NAD^+$/NADH, $NADP^+$/NADPH and $FAD^+$/FADH.

4. The recombinant, artificial or engineered pathway of claim 1, wherein the [cofactor] *first and second cofactors* comprises $NAD^+$/NADH [or] *and* $NADP^+$/NADPH.

5. The recombinant, artificial or engineered pathway of claim 1, wherein the first cofactor-dependent enzyme comprises an NADH or an NADPH dehydrogenase.

6. The recombinant, artificial or engineered pathway of claim 5, wherein the NADH dehydrogenase is a NADH pyruvate dehydrogenase complex.

7. The recombinant, artificial or engineered pathway of claim 6, wherein the NADH pyruvate dehydrogenase complex comprises a pyruvate dehydrogenase subunit a, a pyruvate dehydrogenase subunit b, a dihydrolipoamide acetyltransferase, and a dihydrolipoamide dehydrogenase.

8. The recombinant, artificial or engineered pathway of claim 7, wherein the pyruvate dehydrogenase subunit a comprises a sequence that has at least 90% sequence identity to SEQ ID NO: 1, wherein the pyruvate dehydrogenase subunit b comprises a sequence that has at least 90% sequence identity to SEQ ID NO: 2, wherein the dihydrolipoamide acetyltransferase has at least 90% sequence identity to SEQ ID NO: 3, and wherein the dihydrolipoamide dehydrogenase has at least 90% sequence identity to SEQ ID NO: 5, wherein the complex converts pyruvate to acetyl-CoA.

9. The recombinant, artificial or engineered pathway of claim 7, wherein the pyruvate dehydrogenase subunit a comprises a sequence that has at least 90% sequence identity to SEQ ID NO: 1, wherein the pyruvate dehydrogenase subunit b comprises a sequence that has at least 90% sequence identity to SEQ ID NO: 2, wherein the dihydrolipoamide acetyltransferase has at least 90% sequence identity to SEQ ID NO: 3, and wherein the dihydrolipoamide dehydrogenase has at least 90% sequence identity to SEQ ID NO: 7 and preferentially uses $NADP^+$, wherein the complex converts pyruvate to acetyl-CoA.

10. The recombinant, artificial or engineered pathway of claim 5, wherein the NADPH dehydrogenase is a member of a NADPH pyruvate dehydrogenase complex.

11. The recombinant, artificial or engineered pathway of claim 10, wherein the NADPH pyruvate dehydrogenase complex comprises a pyruvate dehydrogenase subunit a, a pyruvate dehydrogenase subunit b, a dihydrolipoamide acetyltransferase, and a mutant dihydrolipoamide dehydrogenase [the] *that* preferentially uses $NADP^+$.

12. The recombinant, artificial or engineered pathway of claim 1, wherein the NADH or the NADPH oxidase is a NoxE or homolog thereof.

13. The recombinant, artificial or engineered pathway of claim 12, wherein the NADH or the NADPH oxidase comprises a sequence that has at least 50% sequence identity to SEQ ID NO: 10.

14. The recombinant, artificial or engineered pathway of claim 1, wherein the pathway is in a cell-free system.

15. The recombinant, artificial or engineered pathway of claim 1, wherein the pathway is in a living cell.

16. The recombinant, artificial or engineered pathway of claim 1, wherein the recombinant, artificial or engineered pathway produces PHB.

17. The recombinant, artificial or engineered pathway of claim 1, wherein the recombinant, artificial or engineered pathway produces ethanol.

18. The recombinant, artificial or engineered pathway of claim 1, wherein the recombinant, artificial or engineered pathway produces lactate.

19. An enzymatic system comprising a metabolic pathway including a plurality of enzymes for converting a substrate to a product, the metabolic pathway having an unbalanced utilization of reducing/oxidizing cofactors, wherein the enzymatic system comprises

*a first cofactor-dependent enzyme that is capable of converting the substrate to the product, said first cofactor-dependent enzyme producing the unbalanced production of a first cofactor; and*

*a second cofactor-dependent enzyme that uses a second cofactor than the first cofactor-dependent enzyme and that converts the substrate to the product and wherein said second cofactor-dependent enzyme produces an unbalanced production of the second cofactor, and* a metabolic purge valve comprising an NADH pyruvate dehydrogenase and a [NADH/NADPH] *an NADH or an NADPH* oxidase.

20. A recombinant polypeptide comprising a sequence that has at least 99% sequence identity to SEQ ID NO: 5 and comprising the mutations E206V, G207R, A208K, and S213R, wherein the polypeptide has dihydrolipoamide dehydrogenase activity.

* * * * *